US011920147B2

(12) United States Patent
Arts

(10) Patent No.: US 11,920,147 B2
(45) **Date of Patent: *Mar. 5, 2024**

(54) GENOMIC RNA PACKAGING ENHANCER ELEMENT

(71) Applicant: CASE WESTERN RESERVE UNIVERSITY, Cleveland, OH (US)

(72) Inventor: Eric J. Arts, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 946 days.

This patent is subject to a terminal disclaimer.

(21) Appl. No.: 16/168,549

(22) Filed: Oct. 23, 2018

(65) Prior Publication Data

US 2019/0211357 A1 Jul. 11, 2019

Related U.S. Application Data

(63) Continuation of application No. 14/652,335, filed as application No. PCT/US2013/075355 on Dec. 16, 2013, now Pat. No. 10,106,816.

(60) Provisional application No. 61/737,367, filed on Dec. 14, 2012.

(51) Int. Cl.

| | |
|---|---|
| ***C12N 15/86*** | (2006.01) |
| ***C07K 14/005*** | (2006.01) |
| ***C12N 15/63*** | (2006.01) |
| *A61K 48/00* | (2006.01) |

(52) U.S. Cl.

CPC ............ *C12N 15/86* (2013.01); *C07K 14/005* (2013.01); *C12N 2740/15042* (2013.01); *C12N 2740/15052* (2013.01); *C12N 2740/16043* (2013.01); *C12N 2740/16222* (2013.01)

(58) Field of Classification Search

CPC .......... C12N 15/86; C12N 2740/15042; C12N 2740/15052; C12N 2740/16043; C12N 2740/16222

See application file for complete search history.

(56) References Cited

U.S. PATENT DOCUMENTS

| | | | | |
|---|---|---|---|---|
| 6,541,248 B1 | 4/2003 | Kingsman et al. | | |
| 2006/0019393 A1 | 1/2006 | Cannon et al. | | |
| 2012/0027725 A1 * | 2/2012 | Galvin | .................. | C12N 15/86 424/93.2 |

FOREIGN PATENT DOCUMENTS

| | | | | |
|---|---|---|---|---|
| EP | 1337655 B1 | 7/2010 | | |
| WO | WO-9932646 A1 * | 7/1999 | ............. | C12N 15/86 |
| WO | 2007/098326 A1 | 8/2007 | | |

OTHER PUBLICATIONS

Watts et al. Architecture and secondary structure of an entire HIV-1 RNA genome. Nature 460:711-716 plus 3-page Methods; (Year: 2009).*

Chamanian M et al. A cis-Acting element in retroviral genomic RNA links Gag-Pol ribosomal frameshifting to selective viral RNA encapsidation. Cell Host Microbe 13:181-192, 2013.

* cited by examiner

*Primary Examiner* — Quang Nguyen

(74) *Attorney, Agent, or Firm* — TAROLLI, SUNDHEIM, COVELL & TUMMINO, LLP

(57) ABSTRACT

A synthetic lentiviral vector construct comprises a genomic RNA packaging enhancer (GRPE) element and lentiviral nucleic acid sequences sufficient for reverse transcription and packaging in a host cell.

23 Claims, 15 Drawing Sheets

Specification includes a Sequence Listing.

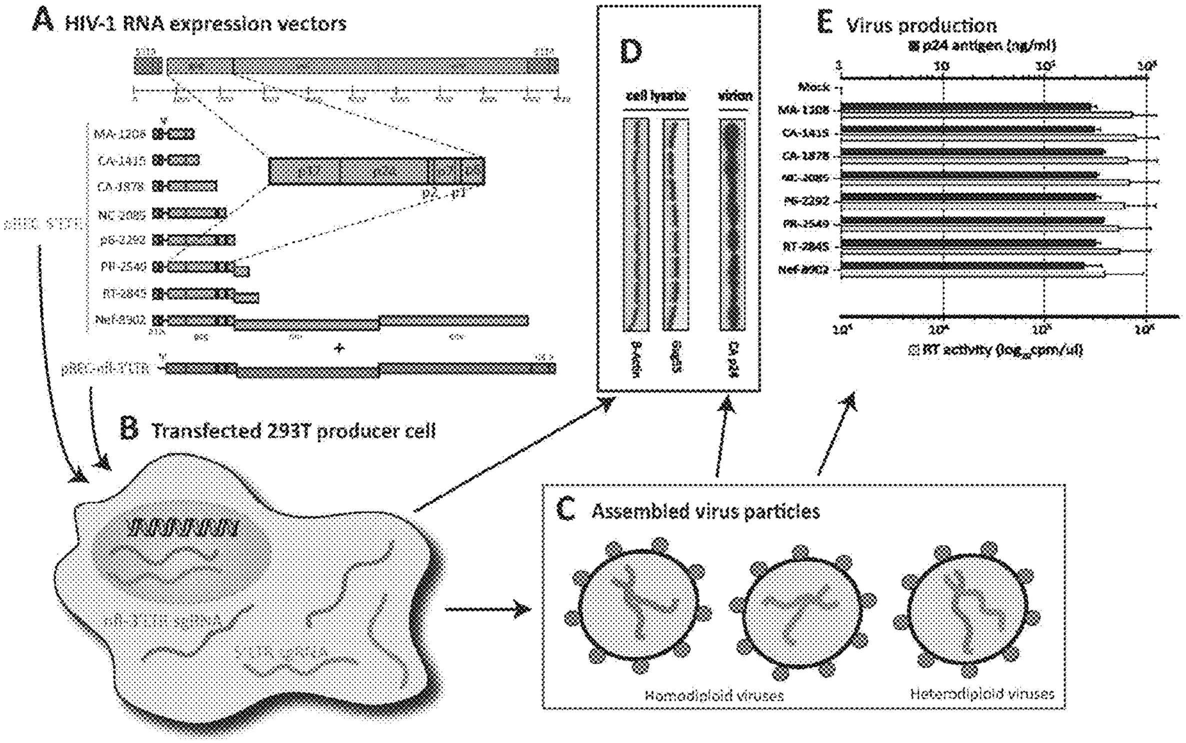
Figs. 1A-E

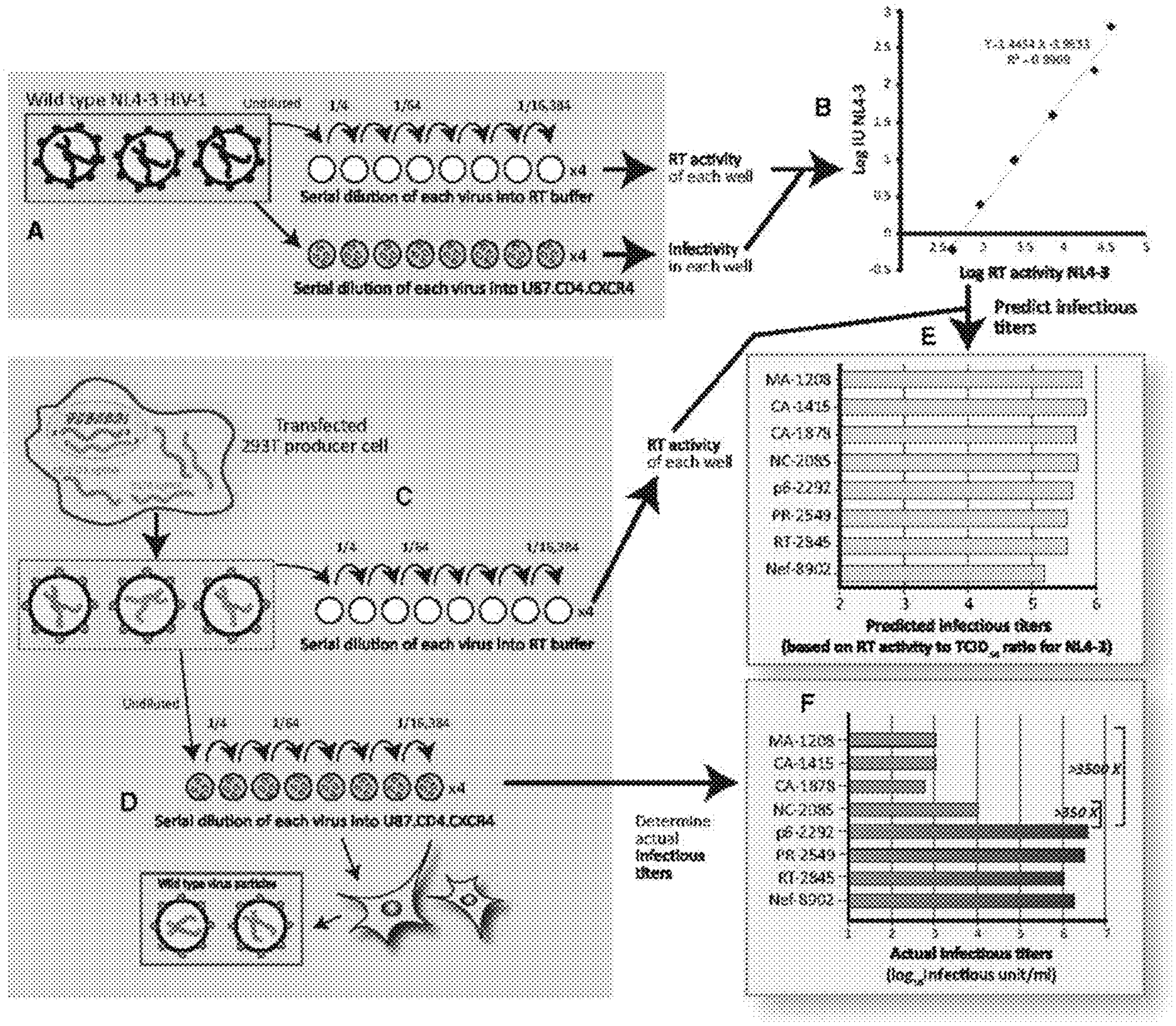
Figs. 2A-F

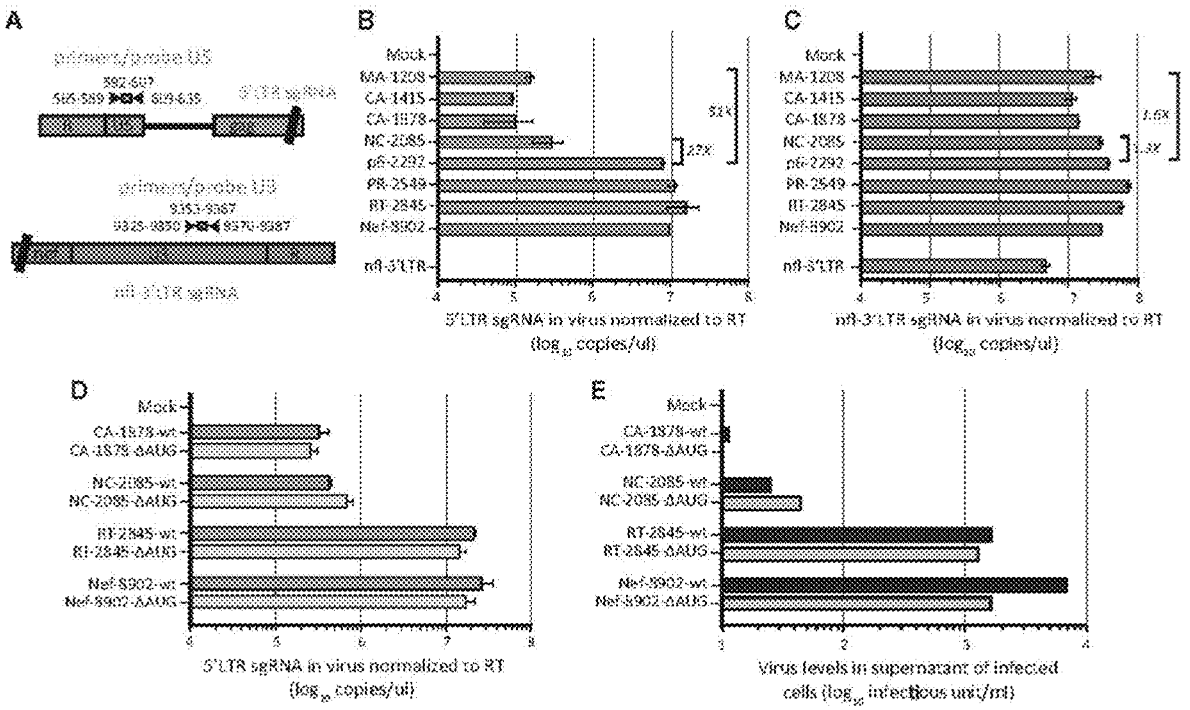
Fig. 3A-E

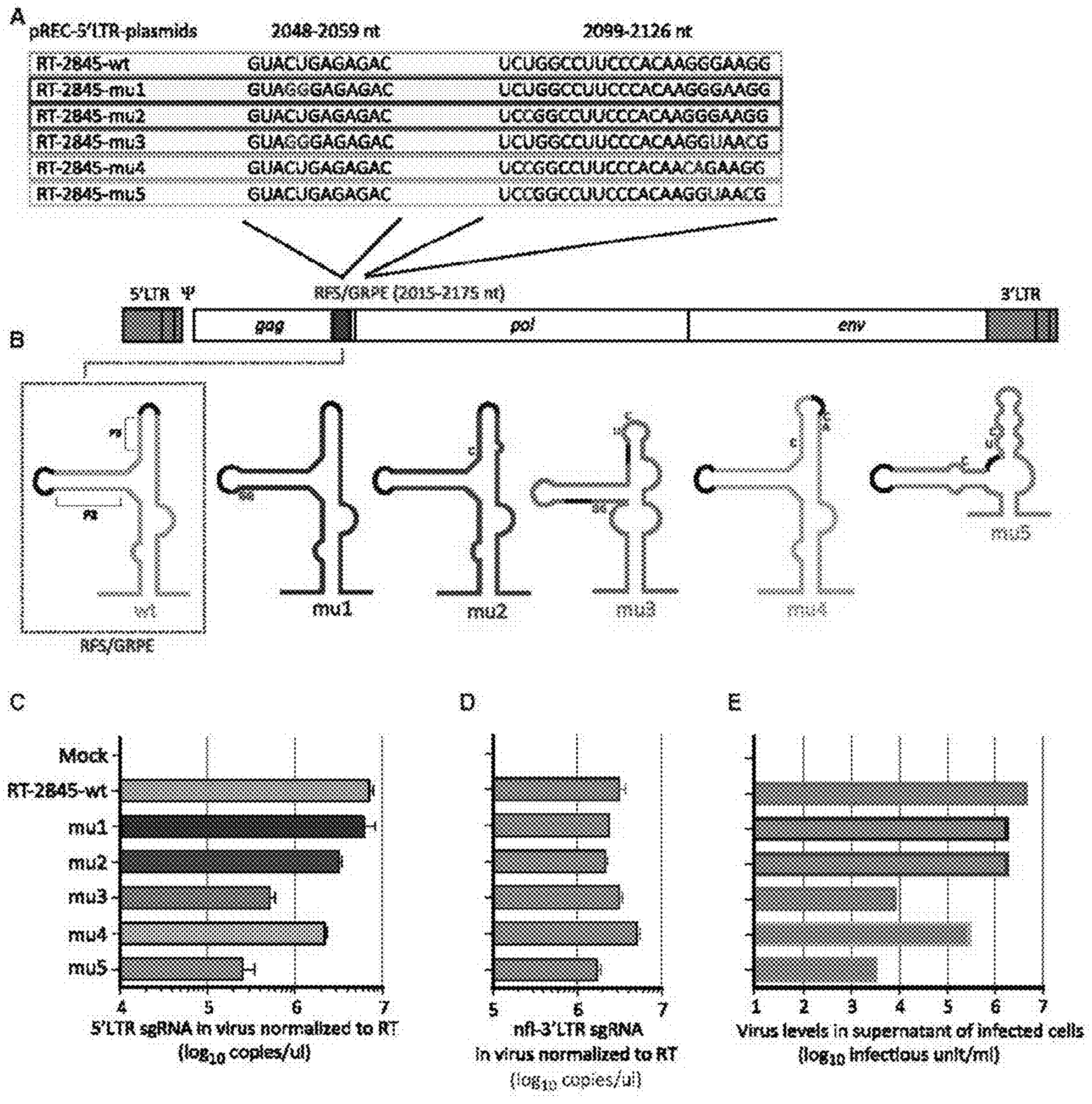
Figs. 5A-E

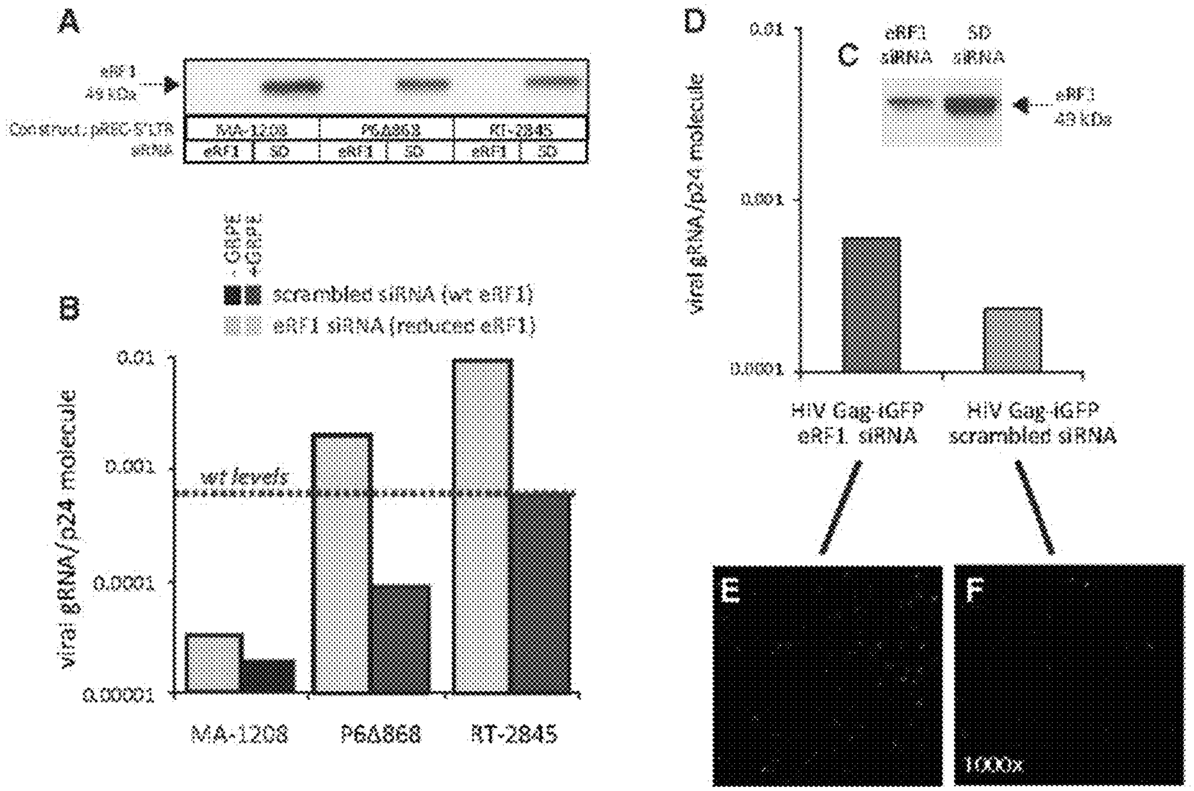
Figs. 6A-F

Figs. 8A-C

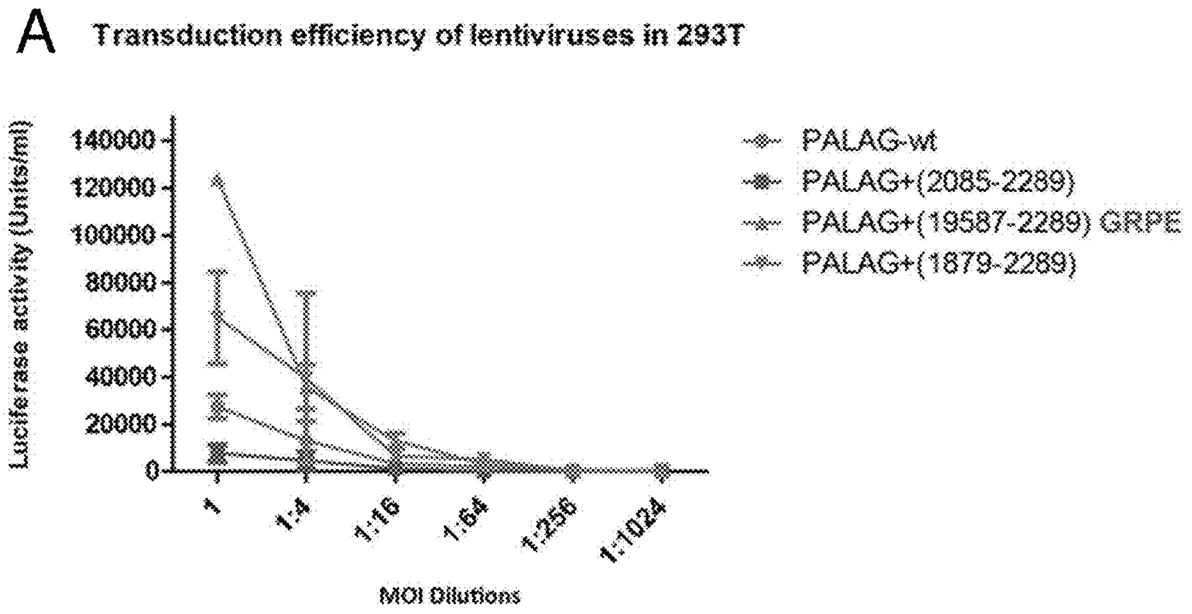
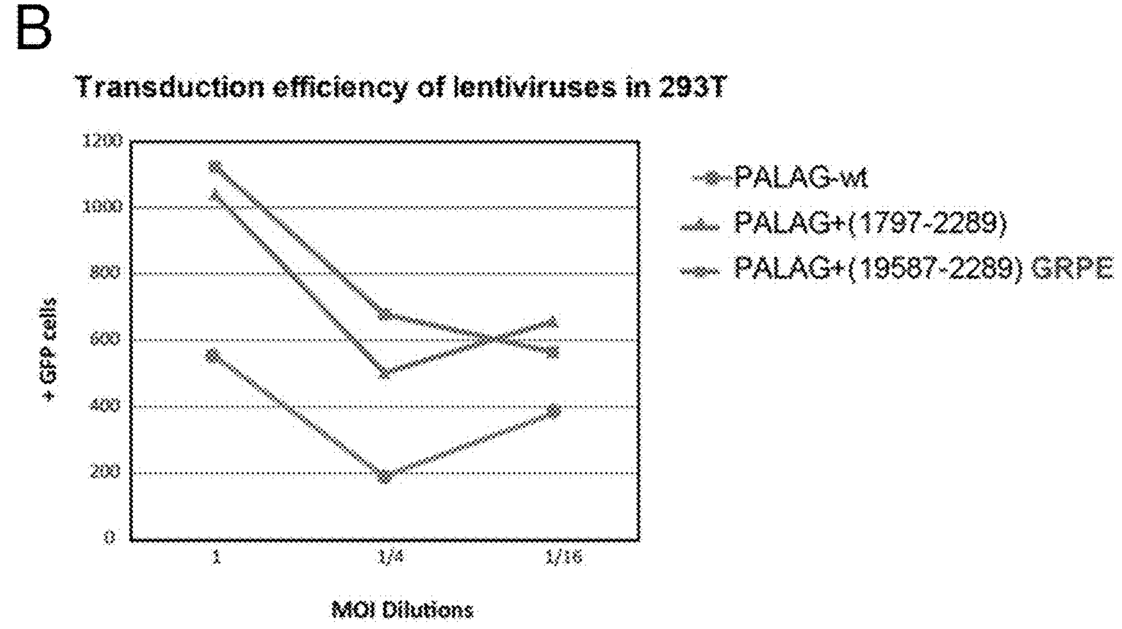
Figs. 11A-B

```
                              SEQUENCE LISTING


<160> NUMBER OF SEQ ID NOS: 3

<210> SEQ ID NO 1
<211> LENGTH: 333
<212> TYPE: DNA
<213> ORGANISM: HIV-1

<400> SEQUENCE: 1

ttaagtgttt caattgtggc aaagaagggc acacagccag aaattgcagg gcccctagga     60

aaaagggctg ttggaaatgt ggaaaggaag gacaccaaat gaaagattgt actgagagac    120

aggctaattt tttagggaag atctggcctt cctacaaggg aaggccaggg aattttcttc    180

agagcagacc agagccaaca gccccaccag aagagagctt caggtctggg gtagagacaa    240

caactccccc tcagaagcag gagccgatag acaaggaact gtatccttta acttccctca    300

ggtcactctt tggcaacgac ccctcgtcac aat                                 333


<210> SEQ ID NO 2
<211> LENGTH: 336
<212> TYPE: DNA
<213> ORGANISM: HIV-1

<400> SEQUENCE: 2

ttaagtgttt caattgtggc aaagaagggc acacagccag aaattgcagg gcccctagga     60

aaaagggctg ttggaaatgt ggaaaggaag gacaccaaat gaaagattgt actgagagac    120

aggctaattt tttagggaag atctggcctt cctacaaggg aaggccaggg aattttcttc    180

agagcagacc agagccaaca gccccaccag aagagagctt caggtctggg gtagagacaa    240

caactccccc tcagaagcag gagccgatag acaaggaact gtatccttta acttccctca    300

ggtcactctt tggcaacgac ccctcgtcac aataaa                              336


<210> SEQ ID NO 3
<211> LENGTH: 209
<212> TYPE: DNA
<213> ORGANISM: HIV-1

<400> SEQUENCE: 3

tttttaggg aagatctggc cttcctacaa gggaaggcca gggaattttc ttcagagcag      60

accagagcca acagccccac cagaagagag cttcaggtct ggggtagaga caacaactcc    120

ccctcagaag caggagccga tagacaagga actgtatcct ttaacttccc tcaggtcact    180

ctttggcaac gacccctcgt cacaataaa                                      209
```

GENOMIC RNA PACKAGING ENHANCER ELEMENT

RELATED APPLICATION

This application claims priority from U.S. Provisional Application No. 61/737,367, filed Dec. 14, 2012, the subject matter of which is incorporated herein by reference in its entirety.

GOVERNMENT FUNDING

This invention was made with government support under AI049170 awarded by the National Institutes of Health. The government has certain rights in the invention.

TECHNICAL FIELD

This application relates generally to nucleic acids comprising a genomic RNA packaging enhancer (GRPE) element of the HIV-1 genome, and more particularly to recombinant retroviruses, such as recombinant lentiviral vectors, comprising a GRPE element and their use in enhancing viral genomic RNA packaging.

BACKGROUND

Retroviral RNA encapsidation is a highly ordered process, by which two full-length genomic (g) RNAs are incorporated into assembling virions. Although a single gRNA template can support retroviral reverse transcription and proviral DNA synthesis, recombination and reassortment of polymorphisms is a hallmark feature of the retrovirus and dependent on a diploid genome. Prior to packaging, intergenomic annealing initiates formation of loose noncovalent dimers of unspliced HIV-1 RNA, which is then selected for encapsidation over the excess host cellular and viral spliced HIV-1 RNAs (~99% of the total cellular RNA). This selectivity is due to the recognition of a cis-acting packaging element within the 5' untranslated region (5'UTR) by the nucleocapsid (NC) domain of the Gag polyprotein via two zinc fingers. Confocal microscopy studies suggest that the capture of gRNA by Gag occurs in a perinuclear/centrosomal site. A single interaction with gRNA may nucleate Gag multimerization during assembly, or multiple Gag proteins may preassemble into oligomeric arrays in the cytoplasm prior to gRNA binding.

Secondary and tertiary structures of retroviral gRNAs in the 5'UTR as well as proximal coding regions are involved in gRNA dimerization, packaging, and translation. In HIV-1, the canonical packaging signal (also referred to as psi or $\psi$) contains four stem loops (SL1-SL4) located downstream of the primer binding site (PBS) and extending into the 50 terminus of gag coding sequences. In particular, SL1 contains the dimerization initiation site (DIS) which forms the kissing loop for gRNA dimerization. Both SL2 (containing the splice donor site) and SL3 have high affinity for NC, but only SL3 is recognized as the core packaging element containing the highly conserved GGAG NC-binding sequence. In complex retroviruses such as HIV-1, gRNA packaging and dimerization signals map to multiple sequences in both LTRs and the 5' end of gag, including the trans-activating-responsive (TAR) stem loop and PBS. Despite attempts to define the complete HIV-1 gRNA packaging signal, the relative role of each sequence within HIV-1 genome has remained debatable.

SUMMARY

Embodiments described herein relate to a genomic RNA packaging enhancer (GRPE) element of HIV-1 RNA genome and synthetic, artificial, and/or recombinant lentiviral vectors that include a GRPE element as well as their use in methods of delivering transgenic material to increase viral genomic RNA packaging in a transduced or infected cell. In some embodiments, a recombinant lentiviral vector construct includes a nucleic acid that comprises a GRPE element and lentiviral nucleic acid sequences sufficient for reverse transcription and packaging in a transduced cell. The GRPE element can include a nucleic acid sequence encoding the P2 and P3 stem loops in the gag p1-p6 domain of the HIV-1 RNA wild-type genome. In other embodiments, the GRPE element can include a nucleic acid sequence having at least 80%, at least 85%, at least 90%, at least 95%, or at least 98% sequence identity to SEQ ID NO: 1 or SEQ ID NO: 2.

Other embodiments described herein relate to a pharmaceutical composition that includes a recombinant lentiviral vector construct. The recombinant lentriviral construct includes a nucleic acid that comprises a GRPE element and lentiviral nucleic acid sequences sufficient for reverse transcription and packaging in a transduced or infected cell. The GRPE element can include a nucleic acid sequence encoding the P2 and P3 stem loops in the gag p1-p6 domain of the HIV-1 RNA wild-type genome. In other embodiments, the GRPE element can include a nucleic acid sequence having at least 80%, at least 85%, at least 90%, at least 95%, or at least 98% sequence identity to SEQ ID NO: 1 or SEQ ID NO: 2.

Yet other embodiments relate to a method of increasing or enhancing gRNA packaging in cells transfected with a recombinant lentiviral construct. The method includes constructing a recombinant lentiviral vector construct that includes a nucleic acid that comprises a GRPE element and lentiviral nucleic acid sequences sufficient for reverse transcription and packaging in a transduced or infected cell. The GRPE element can include a nucleic acid sequence encoding the P2 and P3 stem loops in the gag p1-p6 domain of the HIV-1 RNA wild-type genome. In other embodiments, the GRPE element can include a nucleic acid sequence having at least 80%, at least 85%, at least 90%, at least 95%, or at least 98% sequence identity to SEQ ID NO: 1 or SEQ ID NO: 2.

Still other embodiments relate to a method for enhancing transduction efficiency of cells using lentiviral vector construct. The method includes constructing a recombinant lentiviral vector construct that includes a nucleic acid that comprises a GRPE element and lentiviral nucleic acid sequences sufficient for reverse transcription and packaging in a transduced or infected cell. The recombinant lentiviral vector construct can then be administered to a first cell. The presence of the GRPE element increases or enhances the viral gRNA packaging in lentiviral particles released from the first cell. The increased or enhanced viral gRNA packaging is positively correlated to an increase in the transduction efficiency when the lentiviral particles are administered to infected second cells. The GRPE element can include a nucleic acid sequence encoding the P2 and P3 stem loops in the gag p1-p6 domain of the HIV-1 RNA wild-type genome. In other embodiments, the GRPE element can include the nucleic acid sequence having at least 80%, at least 85%, at least 90%, at least 95%, or at least 98% sequence identity to SEQ ID NO: 1 or SEQ ID NO: 2.

BRIEF DESCRIPTION OF THE DRAWINGS

FIGS. 1(A-E) illustrate schematic drawings and graphs showing complementation system used for packaging studies and infectious virus production. (A) Series of pREC-5'LTR HIV-1 vector were constructed to express incremental lengths of HIV-1 subgenomic (sg) RNA. The plasmid harbors the 5'LTR followed by various HIV-1 coding sequence. The pREC-nfl-3'LTR (near full length of nfl) HIV-1 vector lacks the 5'LTR and is used to cotransfect 293T cells and complement the pREC-5'LTR. (B) Both vectors express 5'-capped, 3' poly(A) HIV-1 mRNA species for the full complement HIV-1 proteins in the cells and produce virus particles indistinguishable from those derived from transfection with full-length proviral DNA constructs (e.g., pNL4-3). 293T transfectants produce three virus types (C) containing either two 5'LTR sgRNAs (x), two nfl-3'LTR sgRNAs (y), or one 01 each (heterodiploid or xy). At 48 hr posttransfection, virus produced from 293T cells transfected with pREC-nfl-3'LTR and pREC-5'LTR was monitored by western blots using anti-p24 and anti-β actin (as control for cellular protein expression) in cell lysates or in virus-containing supernatants (D). (E) Virus production was also measured in supernatants by measuring RT activity using a radiolabelled assay or by quantifying CA p24 using an antigen capture assay. Data are presented as mean±SEM.

FIGS. 2(A-F) illustrate schematic drawings and graphs comparing the expected and actual infectious titers of virus derived from cotransfected 293T Cells (A) Wild-type NL4-3 HIV-1 was serially diluted (1:4) and used to measure RT activity and to infect U87.CD4.CXCR4. (B) RT activity was plotted against the level of virus production for each dilution to determine a linear regression formula and to obtain as a surrogate of infectious titer. Virus produced from the cotransfected 293T cells was diluted to measure RT activity (C) or to infect U87.CD4.CXCR4 cells (D). (E) provides the estimated infectious titers based on analyses from (B) and (C). The actual TCID50 values (F) were derived from the serial dilution/infections of the U87.CD4.CXCR4 cells (D) using the standard limiting protocol. The values are plotted at $\log_{10}$ infectious units/ml.

FIGS. 3(A-E) illustrate a schematic drawing and graphs showing relative packaging of the HIV-1 subgenomic RNA in virus derived from cotransfected cells pREC-5'LTR plasmids were used to transfect 293T cells along with pREC-nfl-3'LTR. (A) Schematic representation of primers and probes used to specifically PCR amplify and quantify the 5'LTR sgRNA and nfl-3'LTR sgRNA following cDNA synthesis. Viral RNA was extracted from cell-free supernatants of transfected cells. Copy numbers of 5'LTR sgRNA (B) and nfl-3'LTR sgRNA (C) were determined by qRT-PCR, compared to qRTPCR amplification of in vitro transcribed HIV-1 RNA of known copy number (104 to 1010 copies), and presented as relative to the viral RT activity. (D) RNA packaging efficiency was not influenced by deletion of a Gag AUG start codon in the 5'LTR sgRNAs. Gag AUG initiation codon was deleted in the pREC-5'LTR-$CA_{1878}$, $NC_{2085}$, $RT_{2845}$, and $Nef_{8902}$. Viral RNA was extracted from cell-free supernatants of transfected cells. Copy numbers of WT and ΔAUG 5'LTR sgRNAs were determined by qRT-PCR and normalized to the viral RT activity. (E) Virus infectivity was measured by first normalizing for RT activity, serially diluted as described in FIG. 2D, and then added to U87.CD4.CXCR4 cells, i.e., a standard $TCID_{50}$ assay. The level of infectious virus is presented as $\log_{10}$ infectious units/ml. Data in (B)-(D) are presented as mean±SEM.

FIGS. 5(A-E) illustrate the role of RNA secondary structure in the GRPE/RFS Region on HIV-1 RNA Packaging (A) Multiple point mutations were introduced to the predicted P2 and P3 stem loops within the GRPE/RFS sequence. (B) The RNA secondary structures in the GRPE/RFS region of these five mutants were predicted by M-fold. The five mutant 5'LTR sgRNA templates were expressed in cotransfected 293T cells. Supernatants from these transfected cells were harvested to measure 5'LTR sgRNA (C) and nfl-3'LTR sgRNA levels (D) by q-RT-PCR. The same virus-containing supernatant was then equalized for RT activity, serially diluted, and used to infect U87.CD4.CXCR4 cells. The relative infectivity, as measured by TCID50 assay, is presented as $\log_{10}$ infectious units/ml (E). Data in (C) and (D) are presented as mean±SEM.

FIGS. 6(A-F) illustrate the effect of eRF1 knockdown on virus production and gRNA Encapsidation A pool of three siRNAs against eRF1 effectively reduces cellular eRF1 expression level by ~70% prior to 293T transfections as indicated by western blot analysis (A) and (C). These siRNAtreated 293T cells were cotransfected with the pREC-nfl-3'LTR along with either pREC-5'$LTRMA_{1208}$, pREC-5'LTR-p6Δ868, or pREC-5'LTR-$RT_{2845}$ or transfected with HIV Gag-iGFP. It is important to note that eRF1 knockdown reduced all protein levels in the cell 2-fold within 72 hr. Virus produced from these siRNA-treated, cotransfected cells was noninfectious for U87.CD4.CXCR4 cells. The 5'LTR sgRNA or NL4-3 gRNA in virus particles was measured by qRT-PCR and presented as relative to p24 antigen content (B) and (D). In the presence of WT levels of eRF1 (SD siRNA treatment), the virus produced from the cotransfected cells harbored approximately 1.6 5'LTR sgRNA copies per 2,000 molecules of p24 (or the estimated size of one HIV-1 particle). With the eRF1 knockdown and the WT pREC-5'LTR-$RT_{2845}$, there are approximately 19 5'LTR sgRNA copies per 2,000 p24 molecules. Virus derived from transfections with the HIV Gag-iGFP molecular clone (E, eRF1 knockdown; F, WT eRF1) was sucrosecushion purified, spread on poly-L-lysine coverslips, and images captured on a Deltavision RT epifluorescent microscope system.

FIGS. 11(A-B) illustrate graphical representations of the transduction efficiency of pLV-mnd-PALAG lentiviral particles in 293T cells in vitro using serial dilution of multiplicity of infection (MOI) measured by: A) luciferease; and B) GFP$^+$ cells.

DETAILED DESCRIPTION

Figure 4A:
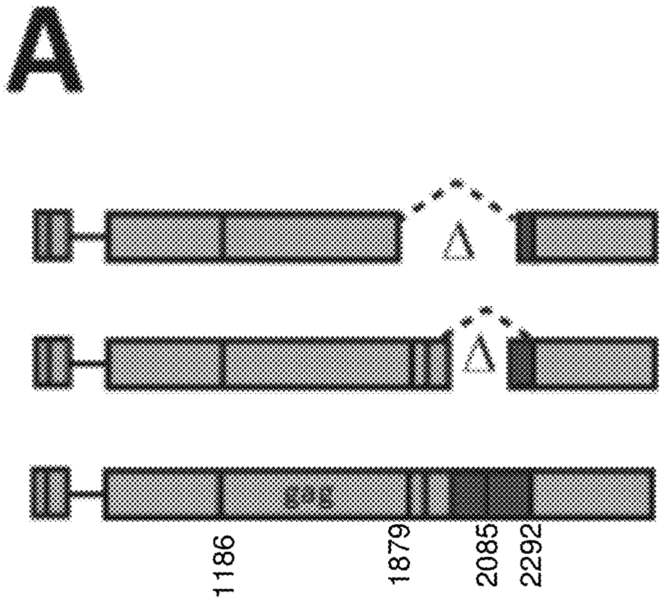
FIGS. 4(A-H) illustrate graphs and schematic drawings showing the effect of deleting the putative GRPE Element and the region separating GRPE and Ψ on packaging of the 5'LTR sgRNA (A) The putative GRPE was deleted as a 1,819-2,251 and 1,956-2,188 nt region in the p1-p6 coding regions of gag within the pREC-5'LTR-$RT_{2845}$, which was then cotransfected with pREC-nfl-3'LTR in 293T cells. A similar GRPE region was also deleted from the WTpNL4-3 construct and cotransfected with the pCMVDR8.91 vector (D). Finally, four regions were deleted separating the putative GRPE from Ψ (E). The gRNAs were quantified in virus particles by qRT-PCR as described in FIG. 3 and presented as copies/μl in (B), (D), and (F) for the 5' LTR sgRNAs (or NL4-3 gRNA) and for the nfl-3'LTR sgRNA. Virus infectivity was measured by first normalizing for RT activity, serially diluting as described in FIG. 2C, and then adding to U87.CD4.CXCR4 cells (FIG. 2D). The level of infectious virus is presented as $\log_{10}$ infectious units/ml in (C) and (G). The structure of the sgRNA was analyzed using SHAPE and presented in (H) using the modeling algorithm RNAstructure. Full-length in vitro-transcribed 5'LTR sgRNA (E) was used for structural probing, but only the region proximal to GRPE/RFS was presented in (H). Data in (B), (D), and (F) are presented as mean±SEM.

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994. The definitions provided herein are to facilitate understanding of certain terms used frequently herein and are not meant to limit the scope of the present invention.

The term "construct" refers to a recombinant nucleotide sequence, generally a recombinant nucleic acid molecule, that has been generated for the purpose of the expression of a specific nucleotide sequence(s), or is to be used in the construction of other recombinant nucleotide sequences.

The term "gene" refers to a nucleic acid comprising a nucleotide sequence that encodes a polypeptide or a biologically active ribonucleic acid (RNA) such as a tRNA, shRNA, miRNA, etc. The nucleic acid can include regulatory elements (e.g., expression control sequences such as promoters, enhancers, an internal ribosome entry site (IRES)) and/or introns. A "gene product" or "expression product" of a gene is an RNA transcribed from the gene (e.g., pre- or post-processing) or a polypeptide encoded by an RNA transcribed from the gene (e.g., pre- or post-modification).

The terms "gene of interest," "nucleotide sequence of interest" and "nucleic acid of interest" refer to any nucleotide or nucleic acid sequence that encodes a protein or other molecule that is desirable for expression in a host cell (e.g., for production of the protein or other biological molecule (e.g., an RNA product) in the target cell). The nucleotide sequence of interest is generally operatively linked to other sequences which are needed for its expression, e.g., a promoter. Further, the sequence itself may be regulatory in nature and thus of interest for expression of biologies in the target cell.

The term "infectious" in reference to a recombinant lentivirus or lentiviral particle, indicates that the lentivirus or lentiviral particle is able to enter cells and to perform at least one of the functions associated with infection by a wild-type lentivirus, e.g., release of the viral genome in the host cell cytoplasm, entry of the viral genome into the nucleus, reverse transcription, and/or integration of the viral genome into the host cell's DNA. It is not intended to indicate that the virus or viral particle is capable of undergoing replication or of completing the viral life cycle. Similarly, the term "infectivity" as used herein in reference to a recombinant lentiviral vector construct, lentivirus or lentiviral particle indicates the ability or the enhanced ability to enter cells and to perform at least one of the functions associated with infection by a wild-type lentivirus. For example, the term "enhanced infectivity" or "enhancing the infectivity" as used herein in reference to a recombinant lentiviral vector construct, lentivirus or lentiviral particle indicates the enhanced or significantly measurable increase in the ability to enter cells and to perform at least one of the functions associated with infection by a wild-type lentivirus compared to a control recombinant lentiviral vector construct, lentivirus or lentiviral particle (e.g., a recombinant lentiviral vector construct, lentivirus or lentiviral particle not comprising a GRPE element).

The term "nucleic acid" refers to polynucleotides such as DNA or RNA. Nucleic acids can be single-stranded, partly or completely, double-stranded, and in some cases partly or completely triple-stranded. Nucleic acids include genomic DNA, cDNA, mRNA, etc. Nucleic acids can be purified from natural sources, produced using recombinant expression systems and optionally purified, chemically synthesized, e.g., iRNA, siRNAs, microRNAs, and ribonucleoproteins. Where appropriate, e.g., in the case of chemically synthesized molecules, nucleic acids can comprise nucleoside analogs such as analogs having chemically modified bases or sugars, backbone modifications, etc. The term "nucleic acid sequence" as used herein can refer to the nucleic acid material itself and is not restricted to the sequence information (i.e., the succession of letters chosen among the five base letters A, G, C, T, or U) that biochemically characterizes a specific nucleic acid, e.g., a DNA or RNA molecule. A nucleic acid sequence is presented in the 5' to 3' direction unless otherwise indicated. The term "nucleic acid segment" is used herein to refer to a nucleic acid sequence that is a portion of a longer nucleic acid sequence.

The terms "operably linked" and "operably associated" refer to a functional relationship between two nucleic acids, wherein the expression, activity, localization, etc., of one of the sequences is controlled by, directed by, regulated by, modulated by, etc., the other nucleic acid. The two nucleic acids are said to be operably linked or operably associated or in operable association. "Operably linked" or "operably associated" can also refer to a relationship between two polypeptides wherein the expression of one of the polypeptides is controlled by, directed by, regulated by, modulated by, etc., the other polypeptide. Typically a first nucleic acid sequence that is operably linked to a second nucleic acid sequence, or a first polypeptide that is operatively linked to a second polypeptide, is covalently linked, either directly or indirectly, to such a sequence, although any effective three-dimensional association is acceptable. One of ordinary skill in the art will appreciate that multiple nucleic acids, or multiple polypeptides, may be operably linked or associated with one another.

The term "plasmid" refers to a circular nucleic acid vector. Plasmids contain an origin of replication that allows many copies of the plasmid to be produced in a bacterial or eukaryotic cell (e.g., 293T producer cell) without integration of the plasmid into the host cell DNA.

The term "promoter" as used herein refers to a recognition site of a DNA strand to which the RNA polymerase binds. The promoter forms an initiation complex with RNA polymerase to initiate and drive transcriptional activity. The complex can be modified by activating sequences termed "enhancers" or inhibitory sequences termed "silencers".

The term "packaging" refers to the process of sequestering (or packaging) a viral genome inside a protein capsid, whereby a virion particle is formed. This process is also known as encapsidation. As used herein, the term "packaging signal" or "packaging sequence" refers to sequences located within the retroviral genome which are required for insertion of the viral RNA into the viral capsid or particle. Several retroviral vectors use the minimal packaging signal (also referred to as the psi "y" sequence) needed for encapsidation of the viral genome. Thus, as used herein, the terms "packaging sequence," "packaging signal," "psi" and the symbol "P" are used in reference to the non-coding sequence required for encapsidation of retroviral RNA strands during viral particle formation. The term includes naturally occurring packaging sequences and also engineered variants thereof. Primary packaging signals of a number of different retroviruses, including lentiviruses, are known in the art.

The term "recombinant" refers to a nucleic acid sequence that comprises portions that do not naturally occur together as part of a single sequence or that have been rearranged relative to a naturally occurring sequence. A recombinant nucleic acid is created by a process that involves the hand of man and/or is generated from a nucleic acid that was created by hand of man (e.g., by one or more cycles of replication, amplification, transcription, etc.). A recombinant virus or viral particle is one that comprises a recombinant nucleic acid. A recombinant cell is one that comprises a recombinant nucleic acid.

The terms "regulatory sequence" and "regulatory element" refer to a nucleic acid sequence that regulates one or more steps in the expression (particularly transcription, but in some cases other events such as splicing or other processing) of nucleic acid sequence(s) with which it is operatively linked. The terms include promoters, enhancers and other transcriptional control elements that direct or enhance transcription of an operatively linked nucleic acid. Regulatory sequences may direct constitutive expression (e.g., expression in most or all cell types under typical physiological conditions in culture or in an organism), cell type specific, lineage specific, or tissue specific expression, and/or regulatable (inducible or repressible) expression.

The term "retrovirus" refers to any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). "Retroviruses" of the invention also include human T cell leukemia viruses, HTLV-1 and HTLV-2, and the lentiviral family of retroviruses, such as Human Immunodeficiency Viruses, HIV-1, HIV-2, simian immnodeficiency virus (SIV), feline immonodeficiency virus (FIV), equine immnodeficiency virus (EIV), and other classes of retroviruses.

Retroviruses are RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions, appears at both the both the 5' and 3' ends of the viral genome. In one embodiment of the invention, the promoter within the LTR, including the 5' LTR, is replaced with a heterologous promoter. Examples of heterologous promoters which can be used include, for example, the cytomegalovirus (CMV) promoter.

The term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells).

The term "hybrid" refers to a vector, LTR or other nucleic acid containing both lentiviral sequences and non-lentiviral retroviral sequences.

The term "transfection" refers to the introduction of foreign DNA into eukaryotic cells. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "transduction" refers to the delivery of a gene(s) using a viral or retroviral vector by means of viral infection rather than by transfection. In preferred embodiments, retroviral vectors are transduced by packaging the vectors into virions prior to contact with a cell. For example, an anti-HIV gene carried by a retroviral vector can be transduced into a cell through infection and provirus integration.

The term "promoter/enhancer" refers to a segment of DNA which contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The term "retroviral vector" refers to a vector containing structural and functional genetic elements that are primarily derived from a retrovirus.

The term "lentiviral vector" refers to a vector containing structural and functional genetic elements outside the LTRs that are primarily derived from a lentivirus.

A retroviral vector is considered a "lentiviral vector" if at least approximately 50% of the retrovirus derived long terminal repeat, LTR (e.g., 5'LTR and/or 3' LTR) and primary packaging sequences (e.g., Ψ) in the vector are derived from a lentivirus and/or if the LTR and primary packaging sequences are sufficient to allow an appropriately sized nucleic acid comprising the sequences to be reverse transcribed and packaged in a mammalian or avian cell that expresses the appropriate lentiviral proteins. Typically, LTR and primary packaging sequences derived from a lentivirus for use in a lentiviral vector of the invention may be at least approximately 50%, approximately 60%, approximately 70%, approximately 80%, approximately 90%, or identical to lentiviral LTR and primary packaging sequences. In certain embodiments of the invention between approximately 90 and approximately 100% of the LTR and primary packaging sequences are derived from a lentivirus. For example, the LTR and primary packaging sequences may be between approximately 90% and approximately 100% identical to lentiviral LTR and primary packaging sequences.

The term "RNAi agent" refers to an at least partly double-stranded RNA having a structure characteristic of molecules that are known in the art to mediate inhibition of gene expression through an RNAi mechanism or an RNA strand comprising at least partially complementary portions that hybridize to one another to form such a structure. When an RNA comprises complementary regions that hybridize with each other, the RNA will be said to self-hybridize. An RNAi agent includes a portion that is substantially complementary to a target nucleic acid sequence or gene. An RNAi agent optionally includes one or more nucleotide analogs or modifications. One of ordinary skill in the art will recognize that RNAi agents that are synthesized in vitro can include ribonucleotides, deoxyribonucleotides, nucleotide analogs, modified nucleotides or backbones, etc., whereas RNAi agents synthesized intracellularly, e.g., encoded by DNA templates, typically consist of RNA, which may be modified following transcription. Of particular interest herein are short RNAi agents, i.e., RNAi agents consisting of one or more strands that hybridize or self-hybridize to form a structure that comprises a duplex portion between about 15-29 nucleotides in length, optionally having one or more mismatched or unpaired nucleotides within the duplex. RNAi agents include short interfering RNAs (siRNAs), short hairpin RNAs (shRNAs), and other RNA species that can be processed intracellularly to produce shRNAs including, but not limited to, RNA species identical to a naturally occurring miRNA precursor or a designed precursor of an miRNA-like RNA.

The terms "vector" and "vector construct" refer to a nucleic acid molecule capable transferring or transporting another passenger DNA or RNA nucleic acid molecule (i.e., a sequence or gene of interest) into a host cell. For instance, either a DNA or RNA vector can be used to derive viral particles. Similarly, a cDNA copy can be made of a viral RNA genome. Alternatively, a cDNA (or viral genomic DNA) moiety can be transcribed in vitro to produce RNA. These techniques are well-known to those skilled in the art, and also are described. The transferred nucleic acid (i.e., a sequence or gene of interest) is generally linked to, e.g., inserted into, the vector nucleic acid molecule. A vector may include sequences that direct autonomous replication in a cell, or may include sequences sufficient to allow integration into host cell DNA. The vector is not a wild-type strain of a virus, inasmuch as it comprises human-made mutations or modifications. Thus, the vector typically is derived from a wild-type viral strain by genetic manipulation (e.g., by addition, deletion, mutation, insertion or other techniques known in the art) to comprise lentiviral vectors, as further described herein. In some embodiments of the present invention, the lentiviral vector constructs for use in a pharmaceutical composition (e.g., a vaccine) comprise those lentiviral vectors in which the lentiviral integrase function has been deleted and/or abrogated by site directed mutagenesis. Useful vectors include, for example, plasmids (typically DNA plasmids, but RNA plasmids are also of use), phages, cosmids, and viral vectors.

The term "viral vector" refers to either a nucleic acid molecule (e.g., a plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s). In particular, the terms "lentiviral vector," "lentiviral expression vector," etc. may be used to refer to lentiviral particles and/or lentiviral transfer plasmids of the invention as described herein. The phrase "essential lentiviral protein" as used herein refers to those viral protein(s), other than envelope protein, that are required for the lentiviral life cycle. Essential lentiviral proteins may include those required for reverse transcription and integration and for the packaging (e.g., encapsidation) of a retroviral genome.

Embodiments described herein relate to a genomic RNA packaging enhancer (GRPE) element of the HIV-1 RNA genome and synthetic, artificial, and/or recombinant lentiviral vectors that include a GRPE element as well as their use in methods of delivering transgenic material to increase viral genomic RNA packaging in a transduced or infected cell. It was found using a system of heterdiploid virus production that efficient gRNA packaging/encapsidation in HIV-1 lentiviral vectors maps to two general regions: Ψ in the 5' UTR and a newly described Genomic RNA Packaging Enhancer element or GRPE element in the gag p1-p6 domain of the HIV-1 RNA genome (~1200 nt downstream from Ψ). Inserting a GRPE element in cis even outside of its wild-type genomic RNA position in lentiviral vectors lacking a GRPE element sequence, increased packaging of viral genomic RNA in nascent viral particles independent of viral protein translation and subsequently increased the infectivity and transduction efficiency of the viral particles themselves when transfected into host cells, e.g., mammalian cell lines. In other words, a transgenic cell generated using a lentiviral vector comprising a GRPE element packages gRNA at a greater level or efficiency in newly formed viral particles compared to a transgenic cell generated using an otherwise identical lentiviral vector not comprising a GRPE element.

In some embodiments, lentiviral vectors described herein include (i) a genomic RNA packaging enhancer (GRPE) element; and (ii) lentiviral nucleic acid sequences sufficient for reverse transcription and packaging in a cell. The lentiviral vector may also include one or more regulatory sequences sufficient to promote transcription of an operably associated sequence of interest (e.g., a gene of interest), which may be inserted downstream of regulatory sequences.

Other embodiments described herein relate to lentiviral transfer plasmids and multi-plasmid systems, wherein at least one of the plasmids comprises a nucleic acid that includes (i) a GRPE element; and (ii) lentiviral sequences sufficient for reverse transcription and packaging.

Still other embodiments relate to lentiviral particles that can include viral Gag, Pol, and Env proteins and a viral genome that comprises (i) a GRPE element; and (ii) sequences sufficient for reverse transcription and packaging in a cell, wherein the sequences are at least in part derived from a lentivirus. For example, lentivirus derived sequences may include a lentiviral R region, a lentiviral 5'LTR region, a lentiviral 3'LTR region, a lentiviral U3 region, a lentiviral U5 region, a lentiviral Ψ sequence, or any combination of the foregoing. It will be appreciated that "nucleic acid sequences sufficient for reverse transcription and packaging" means sequences are sufficient, or at least essential, when present in a nucleic acid in the RNA form but that the sequences may be in the RNA or DNA form in the lentiviral vector, e.g., the nucleic acid component of the vector need not be RNA if the vector is a transfer plasmid.

The GRPE element can be inserted in a variety of different locations in a lentiviral vector. The GRPE element is preferably positioned in operable association with a regulatory sequence in a lentiviral vector of the invention. Typically, the GRPE element is inserted between portions of the vector that comprise sequences for reverse transcription and viral RNA genome packaging. For example, the GPRE may be located in the 3' direction from the Ψ packaging sequence and in the 5' direction from Pol.

In certain embodiments, the advantageous effects of a GRPE element in a lentiviral vector (e.g., increased viral genomic RNA packaging) require the presence of Ψ in the lentiviral vector construct. In some embodiments, the GRPE element may be located near or even directly adjacent to the primary packaging sequence, e.g., P. Alternatively, the GRPE element may be separated from Ψ by a spacer. The spacer may comprise 1-about 1200 nucleotides, and may include any additional packaging sequences outside of GRPE and Ψ.

5' and 3' LTRs may alternatively or optionally include sequence elements that promote transcription (promoter-enhancer elements) and polyadenylation of viral RNA. Therefore, in certain embodiments the lentiviral vector comprises 5' and 3' LTRs or portions thereof and the GRPE is located between the 5' and 3' LTR.

The GRPE element can include a nucleic acid segment derived from the HIV-1 genome and comprises, consists of, or contains the essential elements of a wild-type HIV-1 GRPE element, e.g., minimal sequences of the GRPE element and functional mutations. The GRPE element can be found within the gag p1-p6 domain and overlaps the ribosomal frameshift site of the wild-type HIV-1 RNA genome. On the RNA level, the GRPE element can form two important stem loop structural components. The GRPE structure can be characteristic of a type C three-way junction connective having a stem and two stem loops (P2 and P3). The P2 stem loop, or P2SL, contains a "slippery sequence" flanked at the 3' end by the continuous, P3SL, which is essential for ribosomal frameshifting and the RNA packaging enhancing ability of the GRPE element as identified in the Examples below. Therefore, in certain embodiments, a GRPE element can include the P2 and P3 stem loops on the 3' end of gag.

In some embodiments, a lentiviral vector construct described herein includes a GRPE element that has a nucleic acid sequence that is at least about 40%, at least about 50%, at least about 60%, at least about 70%, at least about 80%, at least about 90%, at least about 95%, or at least about 99% identical to the GRPE element of HIV-1. In some embodiments, the GPRE element includes P2 and P3 stem cell loops with a secondary structure substantially identical or identical to P2SL and P3SL of HIV-1. In other embodiments, a lentiviral vector construct described herein includes a GRPE element that has a nucleic acid sequence that is about 100% identical to the wild-type GRPE element of HIV-1.

By way of example, a GRPE element comprises, consists essentially of, or consists of the nucleic acid sequence corresponding to nt 1958 to nt 2289 of the HIV-1 RNA genome, identified by SEQ ID NO: 1. In another embodiment, a GRPE element comprises, consists essentially of, or consists of the nucleic acid sequence corresponding to nt 1958 to nt 2292 of the HIV-1 RNA genome identified by SEQ ID NO:2. In some embodiments, the GRPE element may comprise, consist essentially of, or consist of a functional GRPE element having at least 60% sequence identity, at least 70% sequence identity, at least 80% sequence, at least 85% sequence identity, identity, at least 90% sequence identity, or at least 95% sequence identity to SEQ ID NO: 1 and/or SEQ ID NO:2. In another embodiment, a GRPE element comprises, consists essentially of, or consists of the nucleic acid sequence corresponding to nt 2085 to nt 2292 of the HIV-1 RNA genome identified by SEQ ID NO:3.

Figure 8:
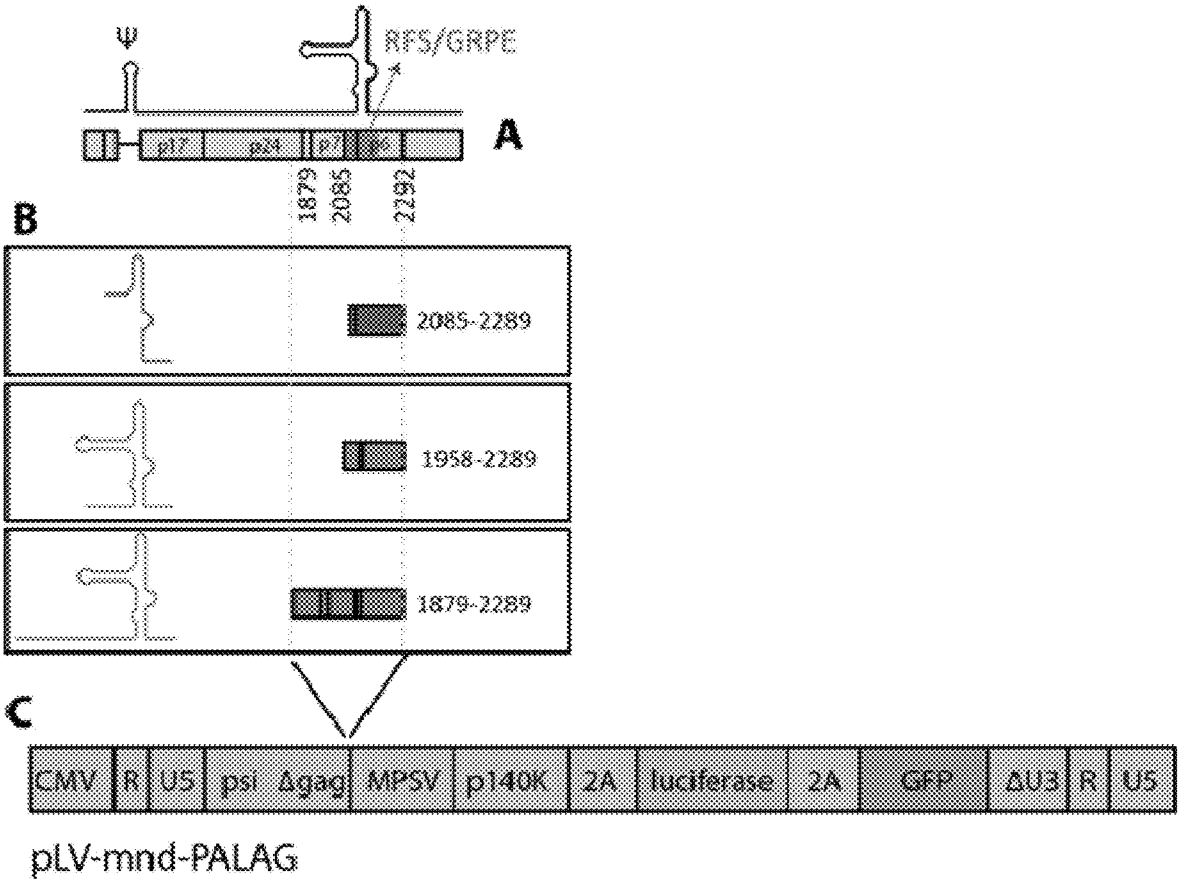
FIGS. 8(A-C) illustrate a schematic representation of: A) Genomic RNA Packaging Enhancer or GRPE element) found within the gag p1-p6 domain of HIV-1 genome and overlapping the ribosomal frameshift site (RFS); B) Three fragments harboring different lengths of GRPE. Fragment 2085-2292 lacks P2SL of GRPE/RFS. However, the other 2 fragments contain complete GRPE/RFS; and C) The construct of bicistronic lentiviral vector plasmid (pLV-mnd-PAGAL) including a MGMT-P140K gene and firefly luciferase gene linked by foot and mouth disease virus (FMDV) 2A cleavage site controlled by an MND promoter.

Additional GRPE elements or fragments, analogues, and mutants of GPRE elements described herein can be identified for use in the compositions and methods described herein. A nucleic acid can be tested in a variety of ways to determine whether it functions as a GRPE element. A nucleic acid functions as a GRPE element if the insertion of the nucleic acid into a lentiviral vector significantly increases or enhances the level or efficiency of gRNA packaging in lentivirus particles released from transfected host cells compared to an otherwise identical lentiviral vector that does not comprise a GRPE element. For example, as shown in FIG. 8 and discussed in Example 2 below, nucleic acid fragments harboring candidate GRPE element sequences can be inserted into a bicistronic lentiviral vector plasmid (pLV-mnd-PAGAL) including a MGMT-P140K resistance gene and a firefly luciferase reporter gene linked by foot and mouth disease virus (FMDV) 2A cleavage site controlled by an MND promoter.

The lentiviral vector can then be used to co-transfect 293T packaging cell along with a packaging plasmid and VSVG envelope vector (see FIG. 9). 48 hours post transfection supernatant and cells were harvested and viral RNA is extracted from the cell-free supernatant and subjected to additional experiments to quantify the level of packaged RNAs in the virions. The observed level of packaged RNAs can then be compared to a control level, such as a negative control level (e.g., the level produced using a wild-type lentiviral vector plasmid that does not comprise a GRPE element) in order to determine if insertion of the candidate nucleic acid significantly increases or enhances the level or efficiency of RNA packaging in lentivirus particles, and therefore if the candidate nucleic acid functions as GRPE.

If desired, portion(s) of a nucleic acid fragment that possess GRPE activity can be narrowed down to a minimal effective region by producing derivatives of the original fragment, in which certain portions are deleted, mutated, or altered, and then testing them in the assay described above. Furthermore, a number of changes can be made in a naturally occurring GRPE element, e.g., using standard molecular biology techniques, without significantly diminishing its activity and possibly even resulting in increased packaging activity. It will thus be appreciated that the term "GRPE element" encompasses both naturally occurring GRPE elements and modified versions thereof that possess gRNA packaging enhancing activity when inserted into lentiviral vector constructs comprising nucleic acid sequences sufficient for reverse transcription and viral RNA genome packaging.

In some embodiments, the lentiviral vectors described herein can be used to produce lentiviral particles that comprise a GRPE element and that these lentiviral particles possess significant advantages in delivering or transferring transgenic material to host cells where it can be replicated and/or expressed. In an exemplary embodiment, transduction efficiency is measured as the number and/or activity level of transduced cells expressing a reporter gene (e.g., luciferace activity or $GFP^+$ cells) in serial dilution of multiplicity of infection (MOI). The term "MOI" as used herein refers to the ratio of the number of infectious virus particles to the number of target cells present in a defined space.

In certain embodiments, the transgenic material may include a sequence of interest or a gene of interest. For example, the transgenic material to be delivered using a lentiviral vector of the present invention may comprise a coding sequence of interest in gene therapy. In certain embodiments, lentiviral particles produced using a lentiviral plasmid vector exhibit enhanced or increased packaging of viral gRNA including sequences of interest inserted therein and subsequently, enhanced or increased infectivity of the viral particles produced from transfected cells when administered to target cells.

In some embodiments, enhanced gRNA packaging and infectivity of viral particles produced from transfected cells can help reduce the high multiplicity of infection (MOI) for transduction with lentiviruses (i.e., the transduction efficiency of the viral particles), which is currently used to raise clinical efficacy and gene expression but also increases the theoretical risk for insertional mutagenesis. Therefore, in certain embodiments, the GPRE element can be used in a method of increasing the transduction efficiency of a lentiviral vector construct. The method can include constructing or forming a lentiviral vector construct that includes the GPRE element and a lentiviral nucleic acid sequence sufficient for reverse transcription and viral RNA genome packaging. The lentiviral vector may further include transgenic material (e.g., a sequence of interest) operably linked to a regulatory sequence to be transferred to host cells. The method also includes transducing or transfecting a first cell with a lentiviral vector construct including the GRPE element. The presence of the GRPE element can increase the viral RNA packaging level in lentiviral particles released from the first cell. When the lentiviral particles infect a second cell or larger group of cells, the increased viral RNA packaging level is correlated with an increase in the transduction efficiency of the lentiviral vector construct.

In certain embodiments, the addition of GRPE to a lentiviral gene delivery vector can enhance lentiviral RNA packaging in viral particles to increase the transduction efficiency in mammalian cells. By way of example, fragments containing HIV-1 sequences corresponding to portions of the GRPE domain were cloned into the HIV-1 based bicistronic pLV-mnd-PALAG lentiviral vector containing a MGMT-P140K gene and a firefly luciferase gene linked by foot and mouth disease virus (FMDV) 2A cleavage site and controlled by an MND promoter. A lentiviral vector containing the complete GRPE domain sequence of HIV-1 (nt 1958 to nt 2289) (SEQ ID NO:1) was co-transfected in 293T packaging cells along with a packaging plasmid and an VSVG envelope vector (FIG. 9) using the pPACK Lentivector Packaging System (SYSTEM BIOSCIENCES, Mountain View, Calif.). 48 hours post transfection supernatant was harvested and the transfection efficiency was monitored by RT activity. Viral RNA was extracted from the cell-free supernatant and subjected to additional experiments to quantify the levels of packaged RNAs in the virions. Results of the viral RNA levels normalized to RT activities, shown in FIG. 10, indicated that addition of GRPE nt 1958-2289 in the pLV-mnd-PALAG plasmid vector increased the packaging of viral RNA compared to control vectors. As illustrated in FIG. 11, a correlation between the increased viral RNA packaging level and the transduction efficiency of such lentiviral vectors was observed. Briefly, serial dilutions of MOI for lentivirus particles produced from transfection were used to infect 293T cells and K562 (human immortalized myelogenous leukemia cells) and transduction efficiency in 293T was monitored 3 days post infection by measuring luciferse and GFP expression using flow cytometry. Results indicated that transduction efficiency in 293T cells of the pLV-mnd-PALAG plasmid vector was increased in lentiviruses containing the complete GRPE domain sequence (SEQ ID NO: 1).

Figure 7:
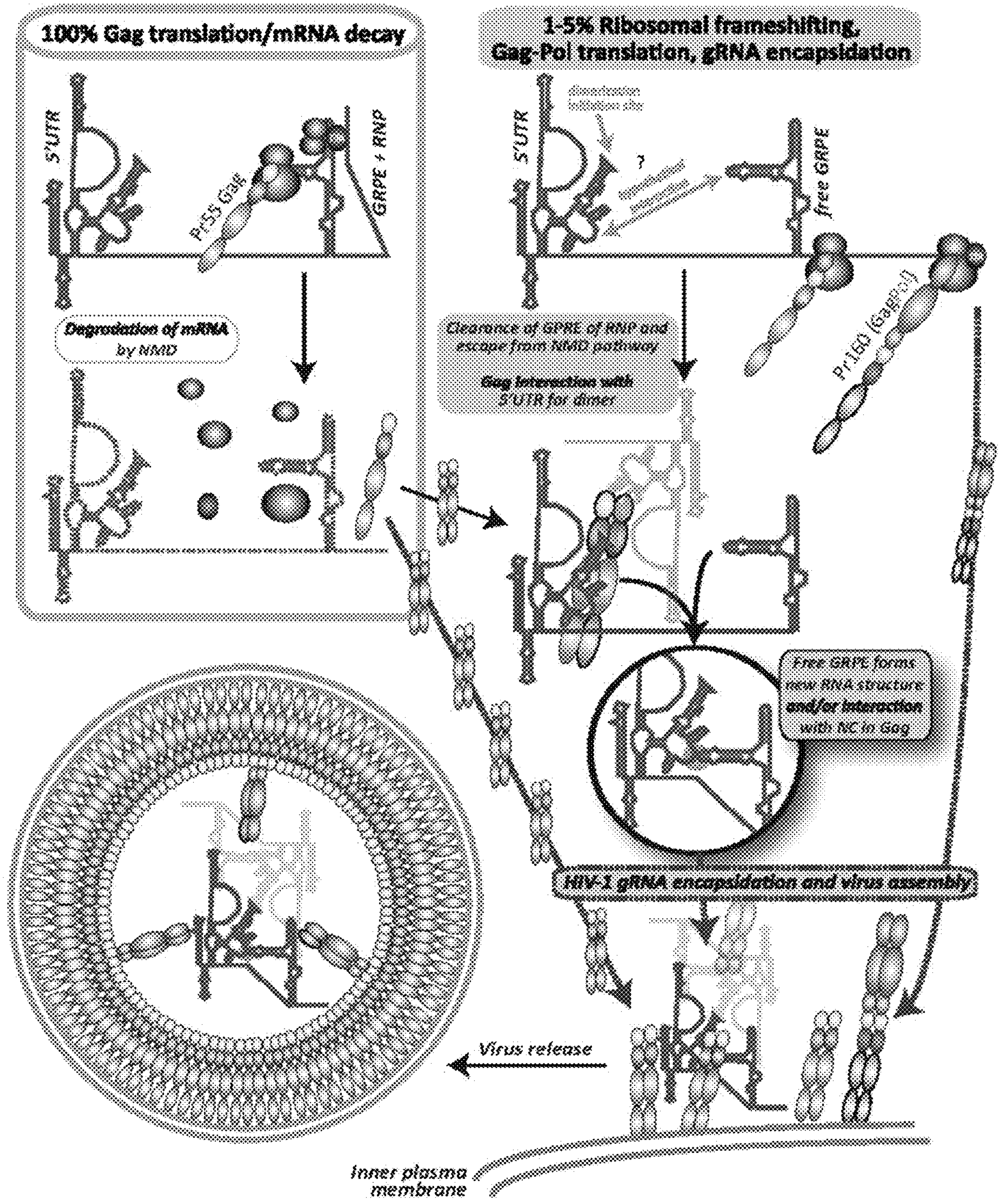
FIG. 7 illustrates a schematic drawing showing a model for translation and packaging of the unspliced HIV-1 RNA.

In other embodiments, the transduction efficiency of viral vectors described herein can be increased by the presence of agents capable of inhibiting specific cellular factors that bind to GRPE and/or inhibit GRPE packaging in a cell. As shown in the Examples below and in FIG. 8A, GRPE overlaps with the ribosomal frameshift site in the HIV-1 genome. FIG. 7 presents a model on the control of HIV-1 translation, ribosomal frameshifting, and gRNA packaging by the GRPE/RFS where an eRF1 complex may form at or near the GRPE/RFS to terminate translation and initiate mRNA degradation by the NMD pathway it is believed that eRF1 interacts with the ribosomal frameshift site and eRF1 depletion. While not wishing to be bound by any theory, it is believed that reducing eRF1 levels maintains a stable unspliced HIV-1 RNA where the GRPE element may be free to participate in higher order RNA interactions (possibly with Ψ) and/or interact with HIV-1 Gag to increase unspliced HIV-1 gRNA packaging in a cell. As discussed further in Example 1 below and in FIG. 6, it was found that reduced eRF1 expression levels using siRNAs in cells subsequently transfected with a viral vector construct including a GRPE element resulted in increased encapsidation of the viral gRNA in viral particles released from transfected cells. It was also found that these viral particles contained ~20 times more gRNA than wild-type virus. When the GRPE element was deleted, the presence or absence of eRF1 had no impact on the low level of gRNA packaging mediated by the 5'UTR.

Therefore, in some aspects viral vectors including a GRPE element and sequences sufficient for reverse transcription and viral gRNA packaging in a cell can be administered to a cell in combination with an eRF1 inhibiting agent in order to increase packaging of viral gRNA in viral particles released by the transfected cell and to increase or enhance the infectivity and transduction efficiency of the viral particles when administered to a second target cell. In certain embodiments, the eRF1 inhibiting agent may include any agent capable of inhibiting eRF1 complex formation, inhibiting eRF1 binding or any interaction with GRPE/RFS, and/or reducing the expression of eRF1 in the cell. For example, a eRF1 inhibiting agent may include an eRF1 siRNA agent (see Kobayashi et al., Identification of a cellular factor that modulates HIV-1 programmed ribosomal frameshifting. *J. Biol Chem.* 285, 19776-19784, the text of which is incorporated herein by reference in its entirety). Additionally or alternatively, an eRF1 inhibiting agent (e.g., an siRNA agent) nucleic acid sequence may be inserted directly into a lentiviral vector construct of the present invention that comprises a GRPE element and sequences sufficient for reverse transcription and viral gRNA packaging in a cell.

Lentiviral particles described herein can include viral Gag, Pol, and Env proteins and a viral genome that comprises a nucleic acid including a GRPE element and sequences sufficient for reverse transcription and packaging may be used to deliver transgenic material to a target cell. The viral genome may further comprise regulatory sequences sufficient to promote transcription of an operably linked sequence of interest.

In certain embodiments, recombinant lentiviral particles are replication-defective, i.e., the viral genome does not encode functional forms of all the proteins necessary for the infective cycle. For example, sequences encoding a structural protein or a protein required for replication may be mutated or disrupted or may be partly or completely deleted and/or replaced by a different nucleic acid sequence, e.g., a nucleic acid sequence of interest that is to be introduced into a target cell. However, sequences required for reverse transcription, integration, and packaging are typically functional.

In some embodiments, lentiviral particles described herein may be produced from a lentiviral plasmid transfer vector using methods known in the art. To produce infectious viral particles that can be used to deliver a recombinant lentiviral genome to host cells and mediate reverse transcription and integration, required viral proteins may be provided in trans. Proteins may be provided by a packaging cell that has been engineered to produce them, e.g., by integrating coding regions of gag, pol, and env genes into the cellular genome, operably linked to suitable regulatory sequences for transcription of the coding region, which may or may not be derived from a virus. Viral genomes transcribed from the vector are packaged with viral enzymes, yielding infectious viral particles. Alternatively or additionally, a helper virus can be used.

Figure 9:
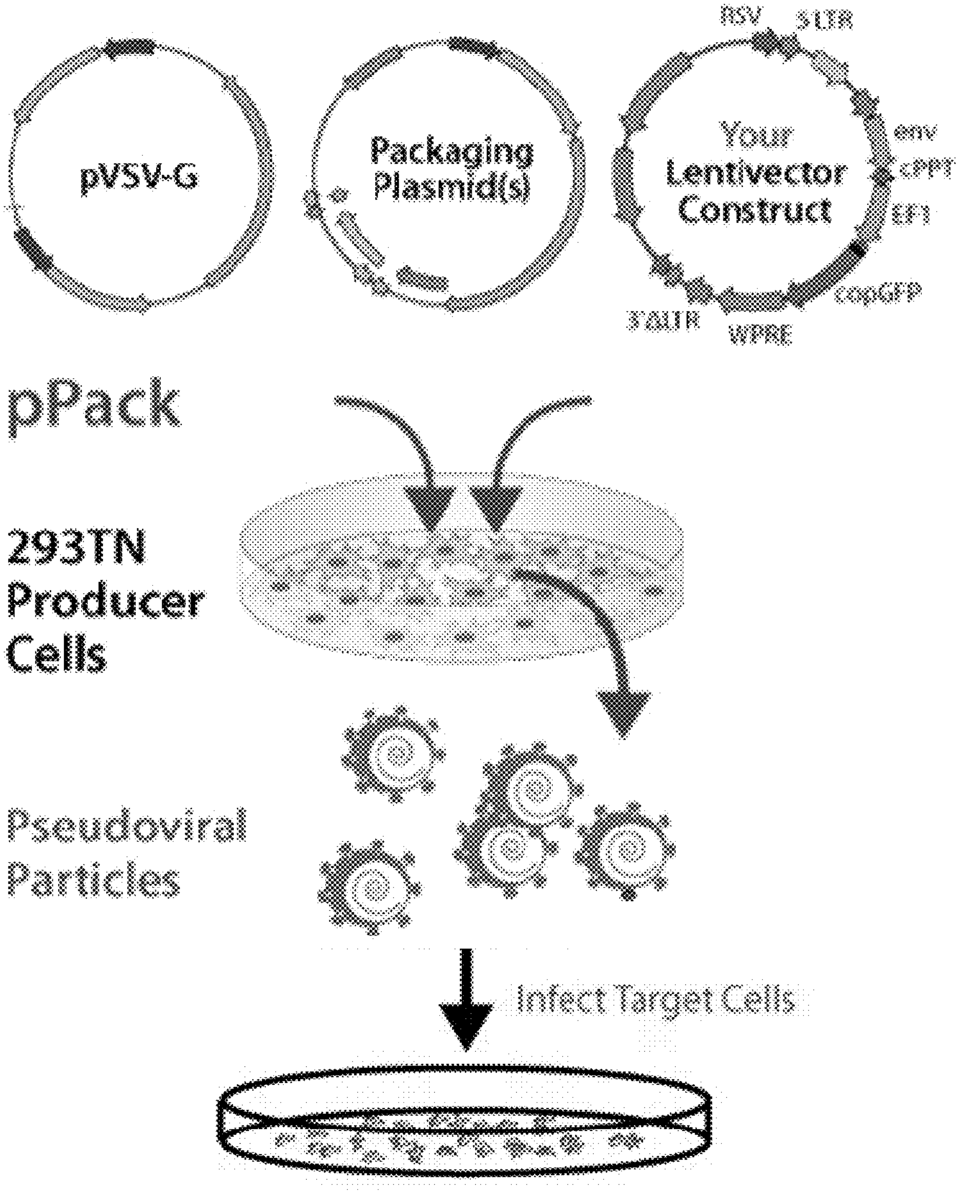
FIG. 9 is a schematic representation of the production of lentiviruses by transfection of 293T cells with 3 plasmids and infection of target cells with the newly released viral particles.

Instead of using packaging cell lines that stably express required viral proteins, cells can be transfected with vectors, e.g., plasmids, that comprise nucleic acid sequences encoding the proteins, operably linked to regulatory sequences for transcription of the coding region. For example, as shown in FIG. 9 and discussed in the examples below, a three vector plasmid system can be used to produce recombinant lentiviral particles comprising a nucleic acid sequence of interest operably linked to a regulatory sequence. The first plasmid is constructed to comprise mutations that prevent lentivirus-mediated transfer of viral genes. The first plasmid (packaging plasmid) comprises a nucleic acid sequence of at least part of a lentiviral genome, wherein the vector (i) encodes at least one essential lentiviral protein and lacks a functional sequence encoding a viral envelope protein; and (ii) lacks a functional packaging signal. The second plasmid (Env-coding plasmid) comprises a nucleic acid sequence of a virus, wherein the vector (i) encodes a viral envelope protein, and (ii) lacks a functional packaging signal. The third plasmid is any of the inventive lentiviral transfer plasmids described herein. Schematic diagrams of relevant portions of representative first and second plasmids (packaging and Env-coding) are presented in FIG. 9. It will be appreciated that a wide variety of regulatory sequences sufficient to direct transcription in eukaryotic cells could be used in the packaging and/or Env-coding plasmid.

Many different types of cell may be used to generate infectious viral particles, provided that the cells are permissive for transcription from the promoters employed. Suitable host cells include, for example, 293 cells and derivatives thereof such as 293T, 293FT (Invitrogen), 293F, NIH3T3 cells and derivatives thereof, etc.

The various proteins need not originate from the same virus. For example, gag and pol genes may be derived from any of a wide variety of retroviruses or lentiviruses, e.g., HIV-1 or HIV-2. Envelope protein can be derived from the same virus from which the other viral proteins are derived, from a different retrovirus or lentivirus, or can include portions of envelope proteins that originate from two or more retroviruses or lentiviruses. Alternatively or additionally, a non-retroviral envelope protein such as the VSVG glycoprotein is used. Use of a non-retroviral envelope protein can significantly reduce or eliminate the possibility of generating replication competent virus during vector manufacturing or after introduction of the vectors into cells and can expand the range of cell types and/or species that virus can enter.

Additional envelope proteins that may be used include ecotropic or amphotropic MLV envelopes, 10A1 envelope, truncated forms of the HIV env, GALV, BAEV, SIV, FeLV-B, RD114, SSAV, Ebola, Sendai, FPV (Fowl plague virus), and influenza virus envelopes. Similarly, genes encoding envelopes from RNA viruses (e.g., RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Birnaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include FIV, FeLV, RSV, VEE, HFVW, WDSV, SFV, Rabies, ALV, BIV, BLV, EBV, CAEV, HTLV, SNV, ChTLV, STLV, MPMV, SMRV, RAV, FuSV, MH2, AEV, AMV, CT10, EIAV. In addition to the above, hybrid envelopes (e.g., envelope comprising regions of more than one of the above), may be employed.

A lentiviral vector comprising a GRPE element can be constructed using any suitable method known in the art using standard methods of molecular biology. For example, a GRPE element can be inserted into an existing plasmid or lentiviral genome. A GRPE element can be inserted into any lentiviral transfer plasmid known in the art or any newly designed lentiviral transfer plasmid or recombinant lentiviral genome. An example of a useful transfer plasmid into which a GRPE element can be inserted includes the bicistronic lentiviral vector plasmid shown in FIG. 8*c*, and variants thereof, e.g., transfer plasmids that comprise different or additional promoters or other regulatory sequences. The resulting lentiviral transfer plasmid may be used to produce lentiviral particles whose genome comprises a GRPE element or for any of a variety of other purposes described herein.

A lentiviral vector typically comprises a nucleic acid that includes cis-acting sequence elements required to support reverse transcription of a lentiviral genome and also cis-acting sequence elements necessary for packaging and integration. These sequences typically include the Psi (Ψ) primary packaging sequence, reverse transcription signals, integration signals, promoters or promoter/enhancers, a polyadenylation sequence, a tRNA binding site, and origin for second strand DNA synthesis. The vector may also include a Rev Response Element (RRE) such as that located at positions nt 7622-nt 8459 in the HIV NL4-3 genome (Genbank accession number AF003887). RREs from other strains of HIV could also be used. Such sequences are readily available from Genbank or from the database with URL hiv-web.lanl.gov/content/index.

Lentiviral vectors and lentiviral particles may include lentiviral sequences derived from any of a wide variety of lentiviruses including, but not limited to, primate lentivirus group viruses such as human immunodeficiency viruses HIV-1 and HIV-2 or simian immunodeficiency virus (SIV); feline lentivirus group viruses such as feline immunodeficiency virus (FIV); ovine/caprine immunodeficiency group viruses such as caprine arthritis encephalitis virus (CAEV); bovine immunodeficiency-like virus (BIV); equine lentivirus group viruses such as equine infectious anemia virus (EIAV); and visna/maedi (VMV) virus. It will be appreciated that each of these viruses exists in multiple variants or strains.

In some embodiments, most or all of the lentiviral sequences are derived from HIV-1. However, it is to be understood that many different sources of lentiviral sequences can be used, and numerous substitutions and alterations in certain of the lentiviral sequences may be accommodated without impairing the ability of a transfer plasmid to perform the functions described herein. Such variations are within the scope of the invention. The ability of any particular lentiviral transfer plasmid construct to transfer nucleic acids to produce a lentiviral particle capable of infecting and transducing cells may readily be tested by methods known in the art.

In certain embodiments, the lentiviral vector can include sub-genomic lentiviral RNA (i.e., sgRNA) and require helper vectors to express viral proteins for particle assembly. A lentiviral vector of the present invention including a sgRNA fragment derived from HIV-1 that includes a GRPE element may be used in a dual gRNA complementation system to enhance the viral gRNA packaging level of the system. An exemplary dual gRNA complementation system is described in commonly owned PCT Publication WO2007/098326, filed Feb. 12, 2007, the text of which is incorporated herein by reference in its entirety as if fully set forth herein. In such a system, dividing the HIV-1 genome into two sub-genomic(sg) RNAs (5'LTR-nfl and nfl-3'LTR sgRNAs) expressed from two co-transfected proviral DNA constructs results in a system where only heterodiploid virus produced by the transfected cells can establish de novo infection following completion of reverse transcription. This system of producing heterodiploid virus can then be used for numerous phenotypic drug sensitivity/fitness assays described in PCT Publication WO2007/098326 as well as additional assays known in the art. For example, phenotypic drug sensitivity/fitness assays on viral particles including a patient-derived pol-env HIV-1 fireluciferase sequence produced using a dual gRNA complementation may be performed in the presence of a candidate antiretroviral drug (ARV) to monitor drug sensitivity of the patient derived virus and a control strain.

In addition, the dual gRNA complementation system can be used to screen for agents capable of inhibiting cellular factors that bind to and/or inhibit GRPE function (e.g., eRF1 inhibiting agents) and in a method of identifying antiretroviral agents capable of binding to and/or inhibiting a GRPE element themselves. Thus, it is further contemplated that a dual gRNA complementation system described herein may be used to identify and/or develop antiretroviral drugs that interfere with the proper functioning of the GRPE/RFS sequence of HIV-1, thereby impairing RNA packaging and HIV-1 replication in an infection.

In certain embodiments, the 5'LTR sgRNA can include a GRPE element. For example, as discussed in Example 1, the minimal CMV promoter in a pREC-5'LTR lentiviral vector including a GRPE element derived from the HIV-1 NL4-3 clone, can express a sgRNA starting from R (nt 456; HXB2 genome numbering) and ending at $p6_{2292}$ on the 3' end of gag. The pREC-5'LTR lentiviral vector including a GRPE element can be co-transfected with a complementing vector pREC-3'LTR-nfl (devoid of 5'LTR) to express a sgRNA starting at the primer binding sequence (PBS) and ending with the 3'LTR (FIG. 1B) where only heterodiplid virus produced by a transfected cell can establish de novo infection following completion of reverse transcription. It is appreciated that in the complementation system the relative packaging or encapsidation of 5'LTR sgRNAs including or not including a GRPE element directly correlated with the level of virus infectivity (compare FIGS. 3B and 2F).

Vectors described herein can also include other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid sequence of interest delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated.

A lentiviral transfer plasmid or the genome of a lentiviral particle typically comprises at least one LTR or portion thereof. In certain embodiments, the lentiviral transfer plasmid or genome comprises two LTRs or portions thereof, wherein the two LTRs or portions thereof flank regulatory sequences that are sufficient to promote transcription of an operably linked nucleic acid. In some embodiments, the LTRs themselves may comprise regulatory sequences such as a promoter. The promoter may be derived from a retroviral LTR, e.g., an HIV or HIV-1 LTR. In some embodiments of the invention the transfer vector includes a self-inactivating (SIN) LTR.

A lentiviral plasmid may include a FLAP element. As used herein, the term "FLAP element" refers to a nucleic acid whose sequence includes the central polypurine tract and central termination sequences (cPPT and CTS) of a retrovirus. Typically the retrovirus is a lentivirus, e.g., HIV-1 or HIV-2. Suitable FLAP elements are described in U.S. Pat. No. 6,682,907. While not wishing to be bound by any theory, the DNA flap may act as a cis-active determinant of lentiviral genome nuclear import and/or may increase the titer of the virus.

In some embodiments, lentiviral vectors comprise any of a variety of posttranscriptional regulatory elements whose presence within a transcript increases expression of nucleic acid of interest at the protein level.

In some embodiments, a lentiviral vector may further comprise an insulator. Insulators are elements that can help to preserve the independent function of genes or transcription units embedded in a genome or genetic context in which their expression may otherwise be influenced by regulatory signals within the genome or genetic context. In the context of the present invention, insulators may contribute to protecting lentivirus-expressed sequences from integration site effects, which may be mediated by cis-acting elements present in genomic DNA and lead to deregulated expression of transferred sequences. An insulator sequence may be inserted into one or both LTRs or elsewhere in the region of the vector that integrates into the cellular genome.

Any of a wide variety of regulatory sequences sufficient to promote transcription of an operably linked nucleic acid sequence of interest may be included in lentiviral vectors of the present invention. A vector may include one, two, or more heterologous promoters or promoter/enhancer regions, where "heterologous" here means that the regulatory sequence is not derived from the same lentivirus as the sequences sufficient for reverse transcription and/or packaging. They may be derived from a eukaryotic organism, from a virus other than a lentivirus, or from a different lentivirus. The regulatory sequences may be in the same or in opposite orientation with respect to each other.

One of ordinary skill in the art will readily be able to select appropriate regulatory sequences depending upon the particular application. For example, sometimes it will be desirable to achieve constitutive, non-tissue specific, high level expression of a heterologous nucleic acid sequence of interest. For such purposes viral promoters or promoter/enhancers such as the SV40 promoter, CMV promoter or promoter/enhancer, etc., may be employed. Mammalian promoters such as the beta-actin promoter, ubiquitin C promoter, elongation factor 1a promoter, tubulin promoter, etc., may also be used. If the vectors are to be used in non-mammalian cells, e.g., avian cells, appropriate promoters for such cells should be selected. It may be desirable to employ tissue-specific promoters to achieve cell type specific, lineage specific or tissue-specific expression of a nucleic acid sequence of interest. For example, it may be desirable to achieve conditional expression in the case of transgenic animals or for therapeutic applications, including gene therapy. In certain embodiments, the promoter may direct transcription in hematopoietic stem cells (HSCs). Therefore, transfer plasmids and lentiviral particles of the invention may be used to achieve constitutive, conditional, reversible, or tissue-specific expression in cells, tissues, or organisms, including transgenic animals.

Some embodiments provide conditional expression of a nucleic acid sequence of interest, e.g., expression is controlled by subjecting a cell, tissue, organism, etc., to a treatment or condition that causes the heterologous nucleic acid to be expressed or that causes an increase or decrease in expression of the heterologous nucleic acid. As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue-specific expression.

The vectors may comprise one or more recombination sites for any of a wide variety of site-specific recombinases. It is to be understood that the target site for a site-specific recombinase is in addition to any site(s) required for integration of the lentiviral genome.

As discussed above, the lentiviral vectors that can include any of a variety of heterologous nucleic acid sequences of interest, preferably operably linked to regulatory sequences sufficient for transcription of the heterologous nucleic acid. In some embodiments, the inserted heterologous sequence may be any gene sequence whose expression produces a gene product which affects cell physiology or phenotype.

According to certain embodiments, the inserted heterologous sequence of interest is a reporter gene sequence. A reporter gene sequence, as used herein, is any gene sequence which, when expressed, results in the production of a protein whose presence or activity can be detected and/or monitored either directly or indirectly in a cell. A wide variety of detectable or selectable markers known to those of skill in the art can be used in the above methods to determine whether any particular nucleic acid functions as a GRPE. Suitable reporter gene sequences include, but are not limited to, sequences encoding chemiluminescent or fluorescent proteins such as green fluorescent protein (GFP) and variants thereof such as enhanced green fluorescent protein (EGFP); cyan fluorescent protein; yellow fluorescent protein; blue fluorescent protein; dsRed or dsRed2, luciferase, aequorin, etc. Additional examples of suitable reporter genes include the gene for enzymes galactokinase, beta-galactosidase, chloramphenicol acetyltransferase, beta-lactamase, etc.

According to certain embodiments, the inserted heterologous sequence of interest is a selectable marker gene sequence, which term is used herein to refer to any gene sequence capable of expressing a protein whose presence permits the selective maintenance and/or propagation of a cell which contains it. Examples of selectable marker genes include gene sequences capable of conferring host resistance to antibiotics (e.g., puromycin, ampicillin, tetracycline, kanamycin, and the like), or of conferring host resistance to amino acid analogues, or of permitting the growth of cells on additional carbon sources or under otherwise impermissible culture conditions. A gene sequence may be both a reporter gene and a selectable marker gene sequence. In general, reporter or selectable marker gene sequences are sufficient to permit the recognition or selection of the plasmid in normal cells.

The heterologous sequence or interest may also comprise the coding sequence of a desired product such as a biologically active protein or polypeptide (e.g., a therapeutically active protein or polypeptide) and/or an immunogenic or antigenic protein or polypeptide. Introduction of the lentiviral vector construct into a suitable cell thus results in expression of the protein or polypeptide by the cell. Alternatively, the heterologous gene sequence of interest may comprise a template for transcription of an antisense RNA, a ribozyme, or, preferably, one or more strands of an RNAi agent such as a short interfering RNA (siRNA) or a short hairpin RNA (shRNA). As described further below, RNAi agents such as siRNAs and shRNAs targeted to cellular transcripts inhibit expression of such transcripts. Introduction of the lentiviral vector into a suitable cell thus results in production of the RNAi agent, which inhibits expression of the target transcript. In general, RNAi agents are capable of reducing target transcript level and/or level of a polypeptide encoded by the target transcript by at least about 2 fold, at least about 5 fold, at least about 10 fold, at least about 25 fold, at least about 50 fold, or to an even greater degree relative to the level that would be present in the absence of the inhibitory RNA. Certain specific RNAi agents are capable of reducing the target transcript level and/or level of a polypeptide encoded by the target transcript by at least about 20%, at least about 30%, at least about 40%, at least about 50%, at least about 60%, at least about 70%, at least about 80%, at least about 90%, or at least about 100%.

Lentiviral vector plasmids and multi-plasmid recombinant lentiviral expression systems may be used to produce infectious, replication-defective lentiviral particles of the invention according to methods known to those skilled in the art, some of which have been mentioned above. In general, lentiviral vectors constructs may be used to produce infectious, replication-defective lentiviral particles in conjunction with any system using any combination of plasmids and/or helper cell lines that provides the appropriate combination of required genes. In the case of the recombinant lentiviral expression system of the invention the methods include (i) transfecting a lentivirus-permissive cell with the three-plasmid lentiviral expression system of the present invention; (ii) producing the lentivirus-derived particles in the transfected cell; and (iii) collecting the virus particles from the cell. The step of transfecting the lentivirus-permissive cell can be carried out according to any suitable means known to those skilled in the art. For example, the three-plasmid expression system described herein may be used to generate lentivirus-derived retroviral vector particles by transient transfection. The plasmids may be introduced into cells by any suitable means, including, but not limited to, calcium phosphate or calcium chloride co-precipitation, DEAE-dextran-mediated transfection, lipofection, injection, electroporation, etc.

Infectious virus particles may be collected using conventional techniques. For example, infectious particles may be collected by cell lysis or by collection of cell culture supernatant, as is known in the art. Optionally, collected virus particles may be purified. Purification techniques are well known to those skilled in the art. Methods for titering virus particles are also well known in the art.

Lentiviral particles may also be introduced into target cells using methods well known in the art. Such methods typically involve incubating cells in an appropriate medium in the presence of lentiviral particles and a reagent such as polybrene that facilitates infection. Cells are maintained under suitable culture conditions for a suitable period of time. Optionally, stable cell lines in which all or a portion of the lentiviral genome is integrated into the cellular genome are generated.

A lentiviral vector construct may be delivered to cells in culture or administered to an animal subject. As used herein, terms such as “introducing,” “delivering,” “administering,” and the like when used in reference to a lentiviral vector of the invention or a composition or cell comprising a lentiviral vector of the invention or comprising nucleic acid sequences derived therefrom refers to any method that provides effective contact between the material to be introduced, delivered, or administered, and the cells whose uptake of the material is desired so that uptake can be achieved. The cells may be in cell culture or in a subject.

Target and/or host cells into which a lentiviral vector of the present invention can be introduced into may be eukaryotic cells, e.g., mammalian or avian cells. According to certain embodiments of the invention a cell is a mouse or human cell. They may be dividing cells or non-dividing cells of any cell type. They may be cells that divide intermittently, e.g., that remain in the GO phase of the cell cycle for extended periods of time (e.g., weeks, months, years), or cells that divide only after being stimulated to do so. The cells may be primary cells, e.g. cells that are isolated from the body of a multicellular organism, which may have undergone one or more cycles of cell division following their isolation (e.g., 1-5 or 1-10 cycles of cell division). The cells may be immortalized cells, e.g., cells capable of continuous and prolonged growth in culture, e.g. they may be capable of undergoing hundreds or thousands of cell division cycles. The cells may be from cell lines, e.g., populations of cells derived from a single progenitor cell. The cells may be stem cells, e.g., embryonic or adult stem cells. The cells may be isolated cells. In certain embodiments of the invention the cell is one that has been administered to a subject.

A target or host cell can be present as a single entity, or can be part of a larger collection of cells. Such a “larger collection of cells” can comprise, for instance, a cell culture (either mixed or pure), a tissue (e.g., endothelial, epithelial, mucosa or other tissue), an organ (e.g., lung, liver, muscle and other organs), an organ system (e.g., circulatory system, respiratory system, gastrointestinal system, urinary system, nervous system, integumentary system or other organ), or an organism (e.g., a bird, mammal, or the like). The organs/tissues/cells being targeted may be of the circulatory system (e.g., including, but not limited to blood, including white blood cells), the mucosal system of the nose, trachea, bronchi, bronchioles, lungs, and the like), gastrointestinal system (e.g., including mouth, pharynx, esophagus, stomach, intestines, salivary glands, pancreas, liver, gallbladder, and others), urinary system (e.g., such as kidneys, ureters, urinary bladder, urethra, and the like), nervous system (e.g., including, but not limited to, brain and spinal cord, and special sense organs, such as the eye) and integumentary system (e.g., skin, epidermis, and cells of subcutaneous or dermal tissue). In some embodiments, the cells being targeted are selected from the group consisting of antigen presenting cells. The target cells need not be normal cells and can be diseased cells. Such diseased cells can be, but are not limited to, tumor cells, infected cells, genetically abnormal cells, or cells in proximity or contact to abnormal tissue such as tumor vascular endothelial cells.

Other embodiments described herein relate to a pharmaceutical composition, or a vaccine, comprising the lentiviral vectors described herein above including a GRPE element and lentiviral nucleic acid sequences sufficient for reverse transcription and viral RNA packaging in a host cell and further comprising a “pharmaceutically acceptable carrier” or “genetic adjuvant.”

In certain embodiments, the pharmaceutical composition can include a GRPE element having SEQ ID NO: 1 or SEQ ID NO:2, a sequence of interest operably linked to a regulatory sequence, lentiviral nucleic acid sequences sufficient for reverse transcription and viral RNA packaging in a host cell of a subject and a pharmaceutically acceptable carrier.

Lentiviral vectors described herein are useful for a wide variety of therapeutic applications. In particular, they are useful in any context for which gene therapy is contemplated. For example, lentiviral vectors comprising a heterologous nucleic acid sequence of interest operably linked to a promoter are useful for any disease or clinical condition associated with reduction or absence of the protein encoded by the heterologous nucleic acid sequence of interest, or any disease or clinical condition that can be effectively treated by augmenting the expression of the encoded protein within the subject.

Inventive compositions may be formulated for delivery by any available route including, but not limited to parenteral (e.g., intravenous), intradermal, subcutaneous, oral (e.g., inhalation), transdermal (topical), transmucosal, rectal, and vaginal. Commonly used routes of delivery include parenteral, transmucosal, rectal, and vaginal.

Inventive pharmaceutical compositions typically include a lentiviral vector in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

In some embodiments, active agents, i.e., a lentiviral vector described herein and/or other agents (e.g., an eRF1 RNAi agent) are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. Liposomes can also be used as pharmaceutically acceptable carriers. These can be prepared according to methods known to those skilled in the art.

In some embodiments, it may be advantageous to formulate compositions in dosage unit form for ease of administration and uniformity of dosage. Dosage unit form as used herein refers to physically discrete units suited as unitary dosages for the subject to be treated; each unit comprising a predetermined quantity of a lentiviral vector calculated to produce the desired therapeutic effect in association with a pharmaceutical carrier.

Pharmaceutical compositions can be administered at various intervals and over different periods of time as required, e.g., one time per week for between about 1 to about 10 weeks; between about 2 to about 8 weeks; between about 3 to about 7 weeks; about 4 weeks; about 5 weeks; about 6 weeks, etc. Pharmaceutical compositions can be administered as a prime/multiple boost protocol. Subsequent administration can be at two weeks, four weeks, one month, two months, six months, or one year and as appropriate regimens to maintain a physiological response (e.g., an immune response) over time.

For certain conditions such as HIV it may be necessary to administer the therapeutic composition on an indefinite basis to keep the disease under control. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a lentiviral vector can include a single treatment or, in many cases, can include a series of treatments.

Exemplary doses for administration of gene therapy vectors and methods for determining suitable doses are known in the art. It is furthermore understood that appropriate doses of a lentiviral vector that encodes an RNAi agent, i.e., a vector that comprises a template for synthesis of one or more RNAs that self-hybridize or hybridize with each other to form an RNAi agent such as an shRNA or siRNA may depend upon the potency of the RNAi agent and may optionally be tailored to the particular recipient, for example, through administration of increasing doses until a preselected desired response is achieved. The appropriate dose level for any particular subject may depend upon a variety of factors including the activity of the specific RNAi agent employed, the age, body weight, general health, gender, and diet of the subject, the time of administration, the route of administration, the rate of excretion, other administered therapeutic agents, and the degree to which it is desired to inhibit gene expression or activity.

Lentiviral gene therapy vectors can be delivered to a subject by, for example, intravenous injection, local administration, or by stereotactic injection. In certain embodiments of the invention, vectors may be delivered orally or inhalationally and may be encapsulated or otherwise manipulated to protect them from degradation, enhance uptake into tissues or cells, etc. Pharmaceutical preparations can include a lentiviral vector in an acceptable diluent, or can comprise a slow release matrix in which a lentiviral vector is imbedded. Alternatively or additionally, where a vector can be produced intact from recombinant cells, as is the case for retroviral or lentiviral vectors as described herein, a pharmaceutical preparation can include one or more cells which produce vectors.

Where the target cell comprises a cell within or proximate a tissue being treated, the vector can be delivered by direct injection at an amount sufficient for the gene of interest to be expressed to a degree which allows for highly effective therapy. By injecting the vector directly into or about the periphery of the target tissue, it is possible to target the vector transfection rather effectively, and to minimize loss of the recombinant vectors. This type of injection enables local transfection of a desired number of cells, especially about the targeted tissue, thereby maximizing therapeutic efficacy of gene transfer, and minimizing the possibility of an inflammatory response to viral proteins.

Pharmaceutical compositions comprising a lentiviral vector of the invention can be included in a container, pack, or dispenser, optionally together with instructions for administration.

The following example is for the purpose of illustration only and is not intended to limit the scope of the claims, which are appended hereto.

Example 1

Lentivirus gRNA packaging is important to aspects of HIV-1 replication/pathogenesis, development of drug targets, and enhancement of lentiviral gene delivery or vaccine efficacy. In this Example, the HIV-1 g/mRNA was subdivided into two subgenomic (sg) RNA species where both contain at least ψ required for encapsidation. Only one sgRNA acts as a template for reverse transcription such that mutations/deletions in this RNA can be evaluated for effects on packaging independent of the underlying coding sequence. Using this system, efficient gRNA encapsidation maps to two general regions: ψ in the 5'UTR and a genomic RNA packaging enhancer (or GRPE) element which overlaps with the ribosomal frameshift site (about 1,200 nt downstream from Ψ). A programmed −1 nt ribosome frameshifting occurs at the Gag-Pol ribosomal frameshift signal (RFS) of unspliced HIV-1 mRNA during Gag translation, leading to production of the Gag-Pol precursor protein. Recently, the ribosomal stimulatory hairpin structure in HIV-1 RFS or P3 stem loop (P3SL) as well as stable stem loop (P2 stem loop or P2SL) has been defined by SHAPE RNA structure analyses. In most retroviruses (aside from lentiviruses), a similar region at the 30 terminus of gag forms a pseudoknot that regulates ribosomal pausing. Our findings suggest a coregulation of HIV-1 Gag-Pol translation and gRNA packaging during virus production and assembly.

EXPERIMENTAL PROCEDURES

Plasmids

All plasmids in this study were initially prepared using yeast-based recombination/gap repair system as described.

Transfection and Infection 293T cells were cotransfected with pREC-5'LTR and pREC-nfl-3'LTR plasmids (~3 mg of each plasmid) using FuGENE6 (Roche). Cells and cell-free supernatant were harvested 48 hr posttransfection to measure infectious titers by RT assay and viral protein levels by western blot and p24 antigen capture assays. Cellular and viral RNAs were extracted using the RNeasy kit (QIAGEN) and MagMax (Ambion) kits, respectively, to determine levels of HIV-1 RNA expression and encapsidation. Cytoplasmic and nuclear RNA isolations were performed using the PARIS Kit (Ambion). Correct fractionation of cytoplasmic and nuclear RNA was tested by RT-PCR amplifying the spliced and unspliced actin (respectively) with the OTR580, OTR581, and OTR582 primers.

Quantitative Real-Time PCR

Cell- and virion-associated RNAs were reverse transcribed using specific primer Gag 820-796 for 5'LTR-cDNA and oligo dt primer (Invitrogen) for nfl-3'LTR c-DNA using Superscript III transcriptase (Invitrogen). The ABI PRISM 7000 sequence detection system (Applied Biosystems) was used for qRTPCR amplifications. U5 and U3 target sequences were specifically amplified using primer pairs and probes described in FIG. 3A. 18S ribosomal RNA was amplified as an internal control for cellular RNA with the forward primer human R18.seq-948F and reverse primer human R18.seq-1014R, and detected with probe 6FAM-TAMRA-30. Serial dilutions of plasmid DNA with known copy numbers provided amplification and quantitation controls. For 18 s ribosomal RNA standard, Quantuserial dilution of mRNA Universal 18S Internal Standard (Ambion) was used. Lack of plasmid DNA contamination from transfection of cells was confirmed by a control excluding reverse transcriptase (RT).

RNA Synthesis and Secondary RNA Structure Prediction Analysis

Briefly, in vitro-transcribed RNAs were purified using MEGAclear kit (Ambion), and the size and integrity were checked by denaturing formaldehyde agarose gel electrophoresis. Fluorescently labeled primer (1 ml) was annealed to 2.5 pmols of RNA (Cy5 [+] and Cy5.5 [−]; 8 mM), then reverse transcribed. Primer extension products were analyzed using a Beckman CEQ8000 Genetic Analysis System. Electropherograms were processed using the ShapeFinder software. 1M7 reactivity at each nucleotide position was normalized. Resulting data were introduced to the RNA-structure software as pseudoenergy constraints. Secondary structures were visualized using PseudoViewer web application. M-fold web server was used to predict secondary structures of RNA mutants.

Results

An HIV-1 Replication System Involving Bipartite HIV-1 gRNA where Only One Contributes to the Coding Sequence Research on gRNA packaging has focused primarily on signature RNA sequences or secondary structures in the 5'UTR. Mapping potential RNA packaging elements within the HIV-1 coding region is more challenging, considering confirmatory mutagenesis requires synonymous substitutions to maintain the proteome while altering RNA structure/sequence. For these reasons, we cotransfected the 293T producer cells with the two plasmids expressing two sgRNAs (FIGS. 1A and 1B). Briefly, the minimal CMV promoter in pREC-5'LTR-nfl expresses a sgRNA starting from R (nt 456; HXB2 genome numbering) and ending prior to U3 (Nef-8902nt) with the BGH poly(A) (FIG. 1A), whereas the complementing vector pREC-nfl-3'LTR expresses sgRNA starting at PBS and ending with the U3-R, and HIV-1 poly(A) (termed 3'LTR) (FIGS. 1A and 1B). HIV-1 mRNA expression from the CMV promoter may be slightly reduced from that observed from the HIV-1 LTR promoter, but the 5'LTR-nfl still contains the TAR sequence and is stimulated by Tat. In contrast, the nfl-3'LTR lacks the TAR involved in abortive transcription.

Both sgRNAs from pREC-5'LTR-nfl and pREC-nfl-3'LTR are derived from the NL4-3 clone, harbor Ψ, and can act as mRNA templates for translation of HIV-1 structural proteins in transfected cells. As expected, the truncated 5'LTR sgRNAs did not produce truncated Gag precursor proteins in the cells. If both the 5'LTR-nfl and nfl-3'LTR sgRNAs are encapsidated at equal efficiencies, 50% of the virus particles will be heterodiploid for both sgRNAs (based on Hardy-Weinberg equilibrium X2+Y2+2XY) (FIG. 1C). Due to lack of the U3-R or R-U5 sequences, homodiploid viruses with two copies of 5'LTR-nfl or nfl-3'LTR sgRNAs are unable to complete reverse transcription following de novo entry into a host cell. In contrast, infection with the heterodiploid virus leads to completion of reverse transcription, reconstitution of a full-length wildtype (WT) genome, and proviral DNA integration.

The entire HIV-1 proteome originates from the nfl-3'LTR sgRNA following de novo infection with heterodiploid virus, whereas the 5'LTR-nfl sgRNA only serves a template for tRNALys, 3 binding and synthesis of (−) strand strong-stop DNA. As described below, we have introduced some large deletions, multiple point mutations, and insertions into the coding region of 5'LTR-nfl sgRNA without impacting on RNA packaging or infectivity, whereas other mutations have significant effects. Although the elongating HIV-1 DNA during reverse transcription could jump between the nfl-3'LTR and 5'LTR-nfl sgRNA templates, our high level of infectivity with or without deletions suggests that these recombination events occur at a relatively low frequency (estimated at 10%).

Locating Cis-Acting RNA Elements in the HIV-1 Coding Sequence Necessary for gRNA Encapsidation When pREC-nfl-3'LTR construct was cotransfected with the pCMV_cplt construct (expressing a short sgRNA containing R-U5-PBS-MA), the resulting virus was minimally infectious compared to WT NL4-3 virus (<0.01% infectivity). Although the absolute level of viral RNA was similar to that in WT HIV-1 particles, we determined that this reduced infectivity was attributable to poor packaging of this short 5'LTR sgRNA compared to the nfl-3'LTR sgRNA, despite the fact that both sgRNAs harbored Ψ. As described below, we noticed that WT infectivity was rescued by extending the short 5'LTR sgRNA to a near full-length HIV-1 RNA genome. Based on these observations, we surmised that a previously unrecognized site within the coding sequence of the HIV-1 genome was necessary for efficient RNA packaging.

To crudely map the coding region that contributes to gRNA packaging, we deleted incremental amount of segments from the 3' terminus of proviral genome within the pREC-5'LTR-nfl vector to produce sgRNA (upon transfection) starting with the R-U5 but ending at $Nef_{8902}$, $RT_{2845}$, $PR_{2549}$, $p6_{2292}$, $NC_{2085}$, $CA_{1878}$, $CA_{1415}$, or $MA_{1208}$ (FIG. 1A). For all cotransfections, Gag protein expression in cells and capsid (CA) in viruses were monitored by western blot and ELISA (FIGS. 1D and 1E), and RT activity was measured in the cell-free supernatant (FIG. 1E). Transfections with pREC-nfl-3'LTR alone or cotransfections of the pREC-nfl-3'LTR with the various pREC-5'LTR vectors produced similar amounts of virus based on RT activity (FIG. 1E).

A stock of WT NL4-3 HIV-1 and virus derived from 293T transfections were serially diluted to measure RT activity and to infect U87-CD4-CXCR4 cells (FIGS. 2A, 2C, and 2D). We have previously shown that RT activity of a WT HIV-1 stock is a strong correlate of its infectious titer. Based on the linear regression equation from RT activity versus infectious titer of an NL4-3 virus stock (FIG. 2B), we estimated that each virus from cotransfections would have a similar infectious titer as shown in FIG. 2E. However, the actual serial dilution/infection in U87-CD4-CXCR4 revealed a significant drop in infectious titer with viruses that should have contained the shorter 5'LTR ($NC_{2085}$, $CA_{1878}$, $CA_{1415}$, or $MA_{1208}$) sgRNA compared to the longer 5'LTR ($Nef_{8902}$, $RT_{2845}$, $PR_{2549}$, and $p6_{2292}$) sgRNA (FIG. 2F). Based on this deletion mapping, it appears that a 207 nt sequence within the p1-p6 coding region (between $NC_{2085}$ and $p6_{2292}$ in the 5'LTR sgRNA) was responsible for a >350-fold increase in infectious titers. Even inclusion of another 6,600 nt of sequential HIV-1 genome sequence on the 5'LTR sgRNA (e.g., $Nef_{8902}$; FIG. 1A) failed to further increase infectivity (FIG. 2F). However, shortening the 5'LTR sgRNA from $NC_{2085}$ to $CA_{1878}$ (FIG. 1A) resulted in an additional 10-fold loss of infectivity, i.e., >3,000-fold less infectious than the heterodiploid virus potentially containing the 5'LTR-$p6_{2292}$ and nfl-3'LTR sgRNAs (FIG. 2F).

The GRPE RNA Element is Necessary for Infectivity Via Effects on gRNA Packaging

Since reduced infectivity with the 5'LTR sgRNA truncations was not due to disruption of virus particle formation or release, we suspected that gRNA encapsidation might have been compromised. First, we confirmed that 5'LTR and 3'LTR sgRNAs were efficiently expressed in the cells by showing that cellular-associated viral sgRNA levels, normalized to 18S ribosomal RNA levels, were not affected by the length of the 5'LTR sgRNA. Encapsidation of both sgRNAs can be measured using quantitative reverse transcriptase PCR (qRT-PCR) with 5'LTR- and 3'LTR-specific primers and probes (FIG. 3A). To ensure that viral RNAs were transported from the nucleus, cells were partitioned into cytoplasmic and nuclear fractions. The presence of only spliced b-actin mRNA in the cytoplasmic fraction confirmed efficient separation from the nuclear fraction. There were, however, abundant and similar levels of the unspliced 5'LTR sgRNAs and nfl-3'LTR sgRNA in the cell cytoplasm. HIV-1 Rev binding to the Rev-responsive element (RRE) in the env gene rescues unspliced and partially spliced HIV-1 RNA transcripts from the nucleus for transport to the cytoplasm. It is unlikely that Rev would increase transport of the 5'LTR sgRNA transcripts, because all but 5'LTR-$Nef_{8902}$ sgRNA lack the RRE as well as all known splice acceptor sites. In monotransfections with the pREC-5'LTR vectors and in the absence of Rev (provide by the pREC-nfl-3'LTR), we still detected high levels of unspliced HIV-1 RNA in cytoplasmic fractions (data not shown).

The level of sgRNAs in virus was measured to determine packaging efficiency of the different 5'LTR sgRNAs (FIG. 3B) relative to nfl-3'LTR sgRNA (FIG. 3C). A dramatic shift was observed in 5'LTR sgRNA packaging when this RNA was extended into the p6 region of the gag coding sequence (27-fold increase in packaging of 5'LTR-$p6_{2292}$ sgRNA packaging over 5'LTR-$NC_{2085}$ sgRNA). However, extension of the HIV-1 RNA genome beyond nt 2,292 (to near full length) did not augment gRNA packaging. Relative encapsidation of the different 5'LTR sgRNA directly correlated with the level of virus infectivity (compare FIG. 3B and FIG. 2F). Interestingly, the levels of efficient nfl-3'LTR sgRNAs in virus particles remained relatively constant despite reduced 5'LTR sgRNA packaging (FIG. 3C). As a control, the AUG gag start codon was deleted in some of the 5'LTR sgRNAs (FIGS. 3D and 3E) such that any recombination would result in formation of dead virus, and yet we did not observe an effect on RNA packaging or infectivity, suggesting that this low-frequency recombination was not affecting the primary results with our system.

Reduced HIV-1 Genomic RNA Encapsidation with GRPE Deletion

Figure 4B:
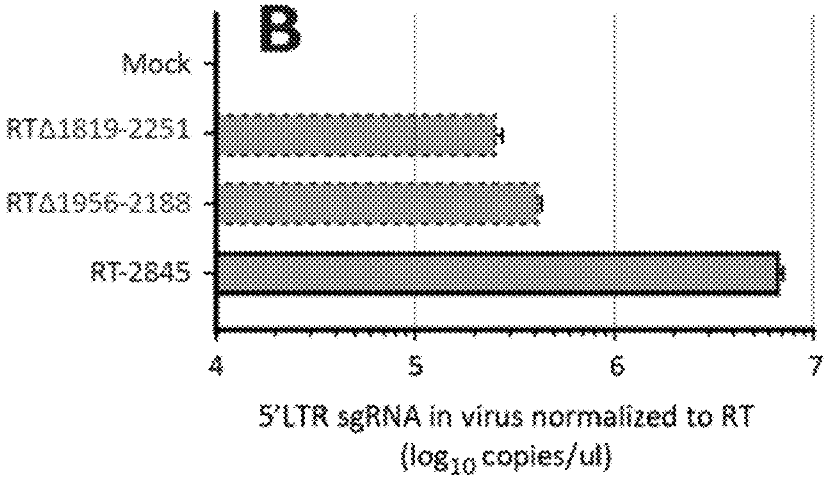
Figure 4C:
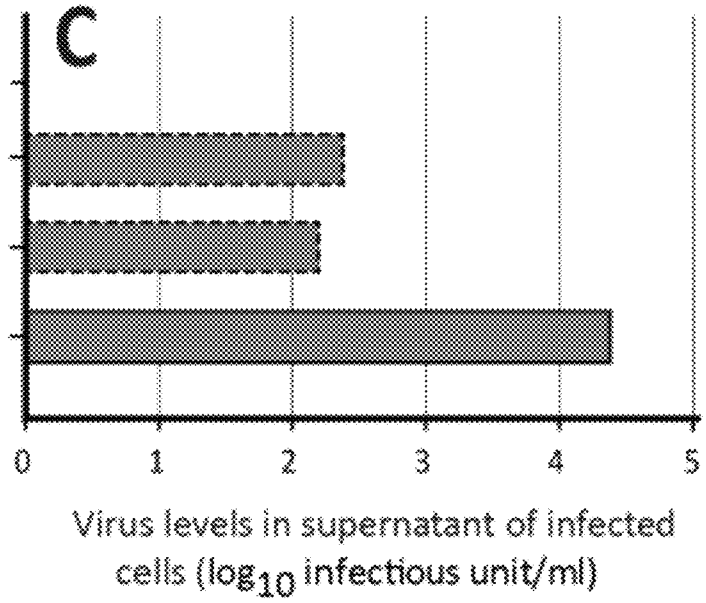

Based on our truncation analyses, we mapped a putative packaging determinant, designated the GRPE, to a 200-400 nt RNA sequence at the 3' end of gag. To confirm the role of the putative GRPE in genome encapsidation, two fragments containing GRPE and surrounding sequences were deleted from pREC-5'LTR-$RT_{2845}$ plasmid (FIG. 4A). Encapsidation of the 5'LTR-$RT_{2845}$ sgRNA with these GRPE deletions was reduced >14-fold (FIG. 4B), while the nfl-3'LTR sgRNAs were encapsidated at similar level. The reduced 5'LTR sgRNA in the absence of the GRPE corresponded to a >80-fold decrease in virus infectivity (FIG. 4C). Based on 3' truncation and deletion analyses, we could map the GRPE to ~200 nt between 1,956 nt and 2,188nt (RNA#1,500 nt-1,732 nt) in the HIV-1 genome which also encompasses RFS. Again, the 5'LTR sgRNA neither contributes appreciably to HIV-1 protein production nor impacts virus particle formation and release, but must be copackaged with the nfl-3'LTR sgRNA for subsequent virus propagation.

Investigating the impact of the GRPE deletion in the full-length HIV-1 construct is problematic due to simultaneous deletion of the Gag open reading frame, which prevents virus production. To compensate, Gag and Gag-Pol proteins were provided in trans from pCMVΔR8.91 helper plasmid cotransfected with WT and ΔGRPE pNL4-3 HIV-1. Due to the 3'-Gag/GRPE deletion, the virus derived from these 293T transfections was limited to a single round of infection and could not be propagated as with the bipartite genome system. Virus from transfections was harvested, equalized for RT activity, and then lysed to measure gRNA content. Virus particles derived from the WT versus pNL4-3ΔGRPE contained 7-fold more gRNA ($p<0.001$) (FIG. 4D).

Positional Dependence of GRPE for gRNA Encapsidation

Figure 4E:
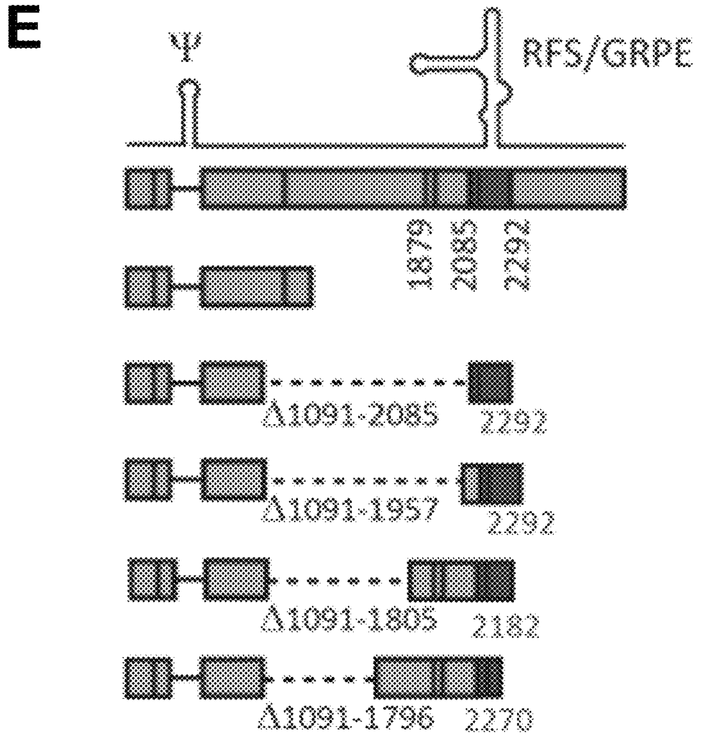
Figure 4D:
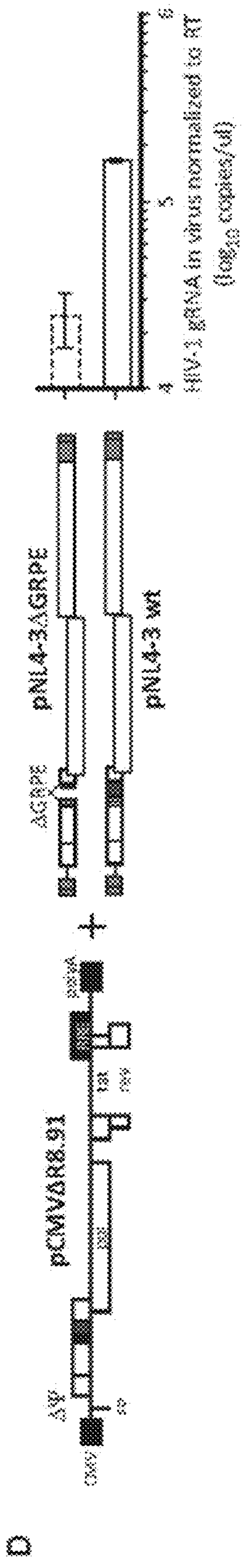
Figure 4F:
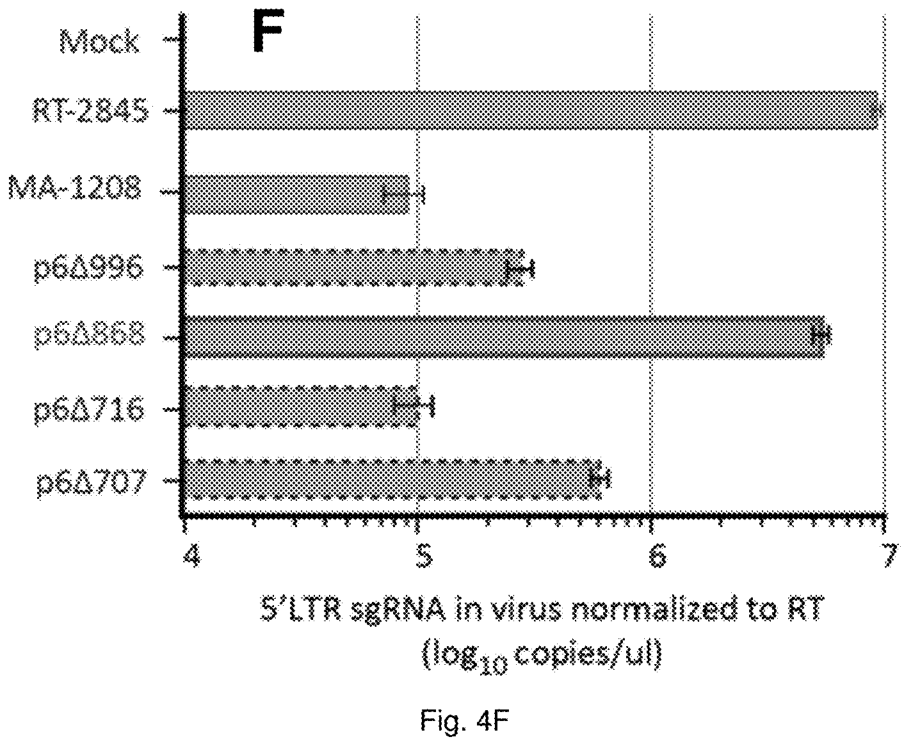
Figure 4G:
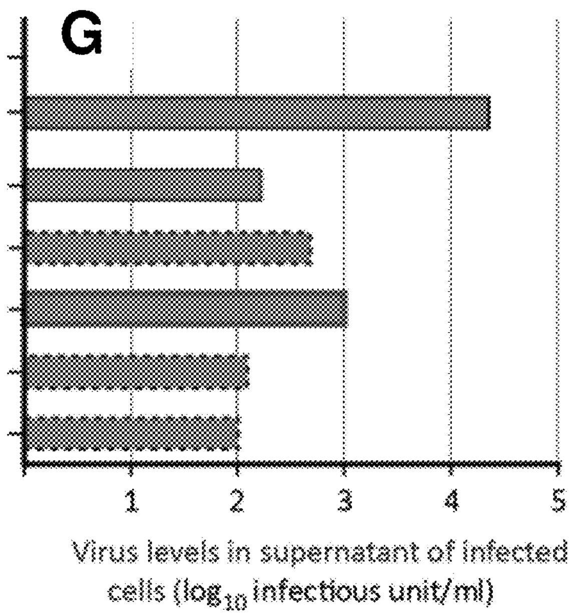
Figure 4H:
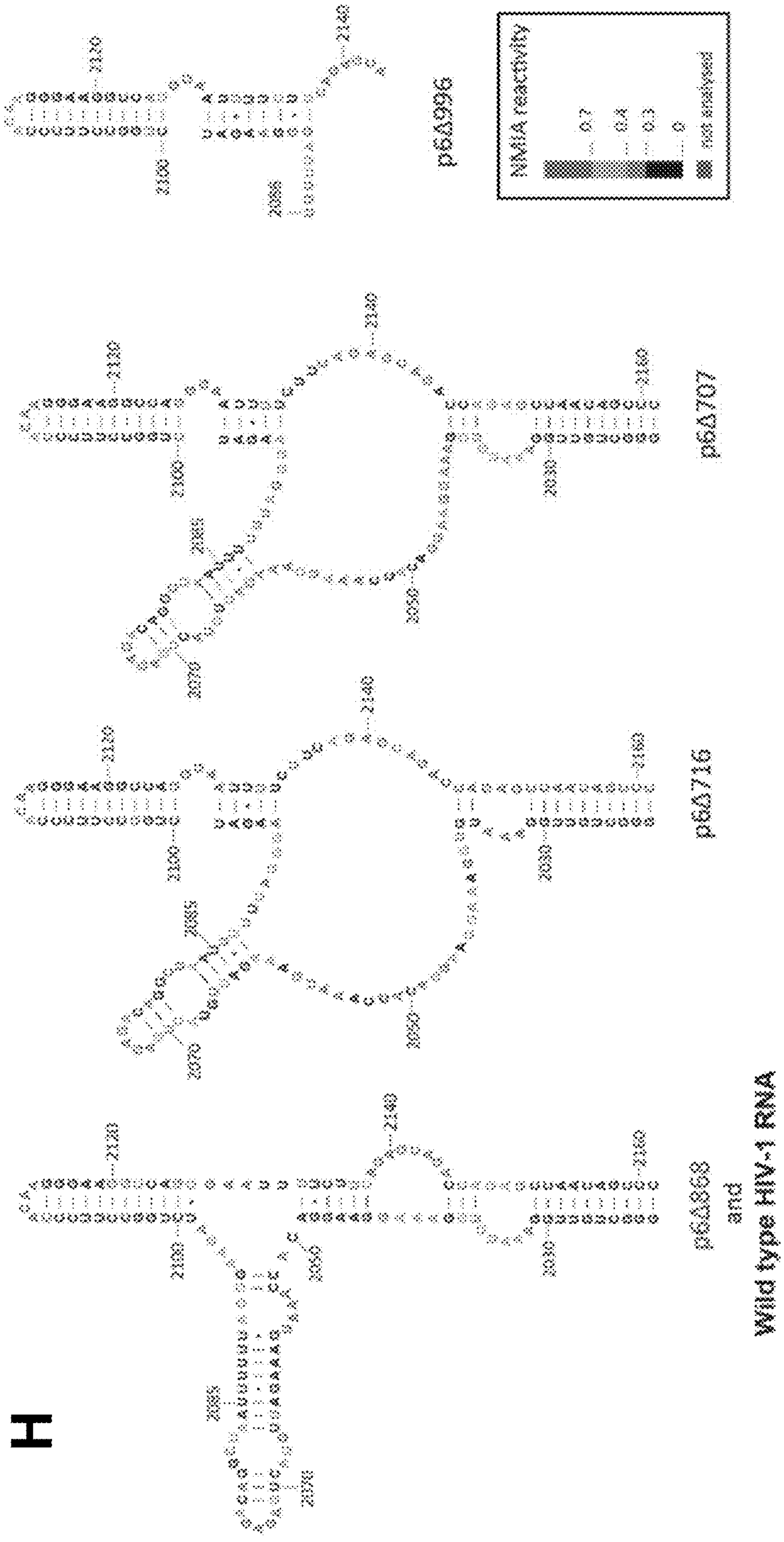

To further map the GRPE, investigate its positional dependence, and determine its minimal structure, sequences between the GRPE and w in the 5'LTR sgRNAs (ending at nucleotides 2,292, 2,270, and 2,183 in p6) were deleted by yeast recombination/gap repair to generate 5'LTR-p6Δ868, Δ716, Δ706, and Δ996 sgRNAs (FIG. 4E). The resulting RNAs lack most of the gag MA/CA/NC coding sequence but retain different p7/p1/p6 coding regions housing the GRPE. Packaging efficiencies and infectivities were investigated with the bipartite genome/complementing system. To better understand the behavior of these gRNA constructs, domains within and around the GRPE were structurally characterized using SHAPE, which involves exposing RNAs to a reactive anhydride (1M7) that selectively acylates ribose 2'-OH moieties within flexible (i.e., usually single-stranded) nucleotides. Sites of chemical modification are subsequently detected as stops during reverse transcription, and the products are fractionated by electrophoresis. RNA secondary structures were predicted by introducing constraints derived from chemical probing data into RNA structure. Full-length in vitro-transcribed 5'LTR sgRNA constructs were used for structural probing, although acylation profiles presented here are restricted to regions involved in RNA packaging (FIG. 4H).

Quantitation of the sgRNAs in virus particles revealed that the 868 nt deletion within the gag coding sequence of 5'LTR sgRNA (FIG. 4E) had WT gRNA packaging levels. However, the 5'LTR-$MA_{1208}$ sgRNA, analogous to removal of the GRPE from 5'LTR-p6Δ868 sgRNA, resulted in a 59-fold decrease in sgRNA packaging (FIG. 4F). Secondary structure analyses of 5'LTRp6Δ868 sgRNA using SHAPE/RNAstructure revealed that the structure of the RFS/GRPE (FIG. 4H) closely resembles the SHAPE-derived RNA structure obtained using gRNA isolated from HIV-1 particles. This structure is characteristic of a type C three-way junction connecting a stem and two stem loops (P2 and P3). P2SL contains the "slippery sequence" flanked at the 3' end by the continuous, P3SL, which is essential for Gag-Pol ribosomal frameshifting.

Surprisingly, deleting a smaller region in 5'LTR-p6Δ706 and 5'LTR-p6Δ716 sgRNA (FIG. 4E) severely reduced sgRNA packaging (FIG. 4F) despite retaining the entire linear GRPE sequence found in 5'LTR-p6Δ868 sgRNA (with WT packaging efficiency). In these cases, the 3' ends of the RNA in 5'LTRp6Δ707 and 5'LTR-p6Δ716 sgRNA were truncated to nucleotides 2,270 and 2,183 (FIG. 4E), respectively. Probing of these two protein-free sgRNAs showed substantial destabilization of P2SL (FIG. 4H). Specifically, the 5'LTR-p6Δ707 and 5'LTRp6Δ716 sgRNA showed high 1M7 reactivity within residues forming P2SL. Moreover, nucleotides 2,044-2,049 show enhanced reactivity compared to 5'LTR-p6Δ868 sgRNA, suggesting they no longer base pair with the segment spanning nucleotides 2,132-2,137 (FIG. 4H). In contrast, nucleotides 2,096-2,098, reactive in the 5'LTR-p6Δ868 sgRNA, were unreactive in these sgRNAs and are instead predicted to be involved in forming an extended, discontinuous P3 hairpin (FIG. 4H). These data suggest that although the GRPE may function independent of sequence context, both the P2 and P3SL must be maintained for enhanced packaging activity. This observation was confirmed by deleting 996 nt of the gag sequence (A1091-2085) in 5'LTR-p6Δ996 sgRNA to remove the linear sequence encoding P2SL, which dramatically reduced packaging (FIG. 4F). Again, the nfl-3'LTR sgRNAs were encapsidated at a stable level. Reduced packaging of the 5'LTR sgRNA with these internal deletions resulted in decreased infectivity of U87.CD4.CXCR4 cells (FIG. 4G). In the case of the 5'LTR-p6Δ868 sgRNA, increased infectivity ($10^3$ IU/ml) was less than expected considering the high level of 5'LTR-p6Δ868 sgRNA packaging (FIG. 4F). As discussed later, intervening RNA sequences (also hidden in the coding sequence) may impact other sgRNA functions aside from encapsidation, such as dimerization, $tRNA^{Lys,3}$ placement, or initiation of reverse transcription.

Effect of GRPE Secondary Structure on gRNA Encapsidation, Dimerization, and Virus Infectivity To further probe the impact of the P2 and P3 stem loops in RNA packaging, we preformed site-directed mutagenesis based on M-fold RNA structure predictions. Mutations (FIG. 5A) causing minor rearrangement in the general structure of both P2 and P3SL (mu1, mu2, and mu4 in FIG. 5B) had minimal effects on 5'LTR sgRNA encapsidation (1.1-, 2.2-, and 3.2-fold, respectively) (FIG. 5C) and only slight losses in infectivity (FIG. 5E). In contrast, when M-fold predicted significant changes to P2 and P3SL with the 4 nt and 3 nt substitutions in mu3 and mu5 sgRNAs (FIGS. 5A and 5B), a 13.5- and 28-fold reduction was observed in packaging which corresponded to a 560- and 1,400-fold loss of infectivity, respectively (FIGS. 5C and 5E). Similar to previous experiments, the levels of nfl-3'LTR sgRNA packaging remained constant with all the mu 5'LTR sgRNAs (FIG. 5D). These studies provided the strongest evidence for the importance of the P2 and P3SL for sgRNA packaging.

Exploring the Relationship Between HIV-1 mRNA Translation and gRNA Packaging

The translation termination factor eRF1 binds to the termination codon, stops translation via interactions with the ribosome, and helps to initiate the nonsense RNA decay (NMD) pathway. Previous studies indicate that siRNA knockdown of eRF1 increased Gag-Pol synthesis relative to Gag, suggesting increased ribosomal frameshifting and loss of infectivity.

To explore the possible role of eRF1 and ribosomal frameshifting on gRNA packaging, we downregulated cellular levels of eRF1 with siRNA (FIG. 6A), but failed to observe an increase in Gag-Pol in virus particles (data not shown). Next, we measured levels of 5'LTR sgRNAs (by qRT-PCR) relative to RT activity (or relative to p24 content of the virus). When eRF1 was depleted with siRNA knockdown, the amount of 5'LTR sgRNA increased >10-fold as compared to virus produced in the presence of scrambled siRNA (FIG. 6B). Based on the assumption of ~2,000 Gag dimers per WT virus particles, knockdown of eRF1 appears to have produced virus particles containing ~15-20 genomic RNAs. We performed the same eRF1 knockdown experiment with an HIV molecular clone (NL4-3 based) that carries a Gag-interdomain green fluorescent protein (iGFP). HIV Gag-iGFP was transfected into 293T cells to produce virus harboring a Gag-GFP fusion. Reductions in eRF1 (FIG. 6C) appear to result in virus particles with more gRNA per Gag molecule (FIG. 6D) as well as brighter fluorescence (compare FIGS. 6E and 6F), suggesting enlarged virus particles containing more of Gag, Gag-Pol, and gRNA.

gRNA Dimerization, GRPE, and Model of gRNA Packaging

FIG. 7 highlights how ribosomal frameshifting and gRNA packaging may be tightly regulated. Dimerization is described as being an early event during gRNA capture/transport and linked to the 5'UTR. To determine the impact of GRPE on gRNA dimerization, we performed in vitro RNA dimerization experiments using 3'LTR and 5'LTR RNAs±GRPE (all containing the DIS). We observed efficient in vitro dimerization of all sgRNAs (either 5'LTR- or 3'LTR-containing RNAs) regardless of the presence or absence of the GRPE. In fact, the shortest 5'LTR RNA (MA-1208) dimerizes with high efficiency (>70% in loose dimers) but cannot be packaged efficiently (>51-fold decrease). Oligonucleotides annealing to DIS could disrupt dimer formation. These in vitro findings may or may not reflect HIV-1 gRNA dimerization in the cell during encapsidation, but our model in FIG. 7 now suggests that GRPE is involved in gRNA encapsidation following loose dimer formation.

As described herein, we show that the GRPE cannot act alone for gRNA packaging but likely involves the y and related 5'UTR sequences.

The importance of the two GRPE stem loops for gRNA packaging was evident with point mutations and deletions of intervening sequences between the GRPE and 5'UTR. Efficient gRNA packaging was maintained with point mutations or deletions that had minor effects on the stability of P2 and P3SL as revealed by SHAPE analyses. Aside from their role in gRNA packaging as described here, these two stem loops are also necessary for ribosomal frameshifting, a mechanism conserved among all lentiviruses. Most retroviruses employ a readthrough translation mechanism whereby a transient/infrequent RNA pseudoknot may stall the ribosome at the UAG stop codon, leading to a glutamine incorporation. Although there is no experimental evidence for involvement of RNA pseudoknots in lentiviral frameshifting, in vitro SHAPE analyses on the static GRPE sequence provide some support for possible pseudoknot involving the P2 and P3SL, but this would also infer a complete unwinding of these two SLs. We also suspect higher-order structures between W and GRPE, but at this stage a series of detailed biochemical studies involving SHAPE and/or high resolution NMR are necessary to support these claims. Nonetheless, biochemical studies presented herein provide evidence for intricate transition events designating an HIV-1 unspliced RNA as (1) an mRNA for Gag translation or (2) an mRNA for Gag-Pol translation and gRNA for encapsidation.

Overlap between the GRPE and the RFS suggested a possible link between translation and gRNA packaging. In relation to translation termination, eRF1 mediates peptidyl-tRNA hydrolysis at the peptidyl transferase center of the ribosome to terminate translation. eRF1 also nucleates a host protein complex involved in 3'UTR sensing and the NMD pathway.

As a preliminary study, we reduced eRF1 expression levels with siRNAs in cells subsequently transfected with our WT and GRPE mutant HIV-1 constructs. Reducing eRF1 levels increased encapsidation of HIV-1 gRNA relative to CA p24 levels in the cell-free supernatant. These virus-like particles may contain >20 times more gRNA than wild-type virus based on an assumption of 2,000 Gag dimers per virus particle. When using a virus containing Gag-iGFP, knockdown of eRF1 appears to mediate production of “large” virus particles with more Gag (brighter virus particles) and more gRNA. Based on these preliminary results and positioning of the GRPE, we propose that Gag-Pol ribosomal frameshifting may prevent the NMD pathway and designate this unspliced HIV-1 mRNA (destined for translation of Gag-Pol) as gRNA for encapsidation. Thus, even slight increases in ribosomal frameshifting and Gag-Pol synthesis could lead to dramatic increases in gRNA levels and release of noninfectious virus particles. FIG. 7 presents a model on the control of HIV-1 translation, ribosomal frameshifting, and gRNA packaging by the GRPE/RFS. A complex involving eRF1 may form at or near the GRPE/RFS during translation. Termination of translation may initiate mRNA degradation by the NMD pathway via accumulation of Up-frameshift protein 1 (Upfl) on the extended 30UTR and thus prevent Gag precursor binding to this RNA for encapsidation. In <5% of translation events on unspliced HIV-1 mRNA, the ribosome may shift −1 nt at the RFS, clear the GRPE, prevent binding Upfl-dependent decay complex, and promote interactions of cytoplasmic poly(A)-binding protein 1 (PABPC1) with eRF1/eRF3 to eventually terminate Gag-Pol translation. This rare event in HIV-1 translation would maintain a stable unspliced HIV-1 RNA where the GRPE may be free to participate in higher-order RNA interactions (possibly with ψ) and/or interact with HIV-1 Gag (or additional cellular factors). Thus, the unspliced mRNA which was used as a template for Gag-Pol translation would also serve as genomic RNA. This model also supports the notion that only a few Gag precursor proteins can bind HIV-1 unspliced mRNA for encapsidation prior to virus assembly leaving the majority of Gag precursors to form the virus core during assembly. Again, this process of virus assembly and correct gRNA encapsidation would be tightly regulated by GRPE, a highly conserved HIV-1 sequence.

Example 2

Optimization of the Lentiviral RNA Packaging and Transduction Efficiency in Hematopoietic Stem Cells (HSC) by Addition of GRPE to the Lentiviral Gene Delivery Vector Using a dual gRNA complementation system, high levels of gRNA packaging were dependent on a cis acting RNA element (termed the Genomic RNA Packaging Enhancer or GRPE element) found within the gag p1-p6 domain and overlapping the ribosomal frameshift site. Three fragments were cloned into the HIV-1 based pLV-mnd-PALAG lentiviral vector (The map is shown in FIG. 8C) in order to investigate the effect of Genomic RNA Packaging Enhancer (GRPE) on a lentiviral packaging level. Enhanced virus production from transfected cells will help reducing the high multiplicity of infection (MOI) for transduction with lentiviruses which is being used currently to raise clinical efficacy, and gene expression which increases the theoretical risk for insertional mutagenesis.

The first fragment contained HIV-1 sequence from nt 2085 to nt 2289, therefore lacking the slippery sequence in P2 stem loop of the GRPE/ribosomal frameshift site (RFS) (FIGS. 8A &B). The second fragment (nt 1958-2289) has the complete GRPE and was shown in a previous study to increase the packaging of genomic RNA significantly (FIGS. 8A &B). The last fragment (nt 1879-2289) also contains the GRPE, but has more sequences upstream of GRPE comparing to fragment 2085-2292. (FIGS. 8A &B)

The lentiviral vectors were used to co-transfect 293T packaging cell along with packaging plasmid and VSVG envelope vector (FIG. 9).

Figure 10:
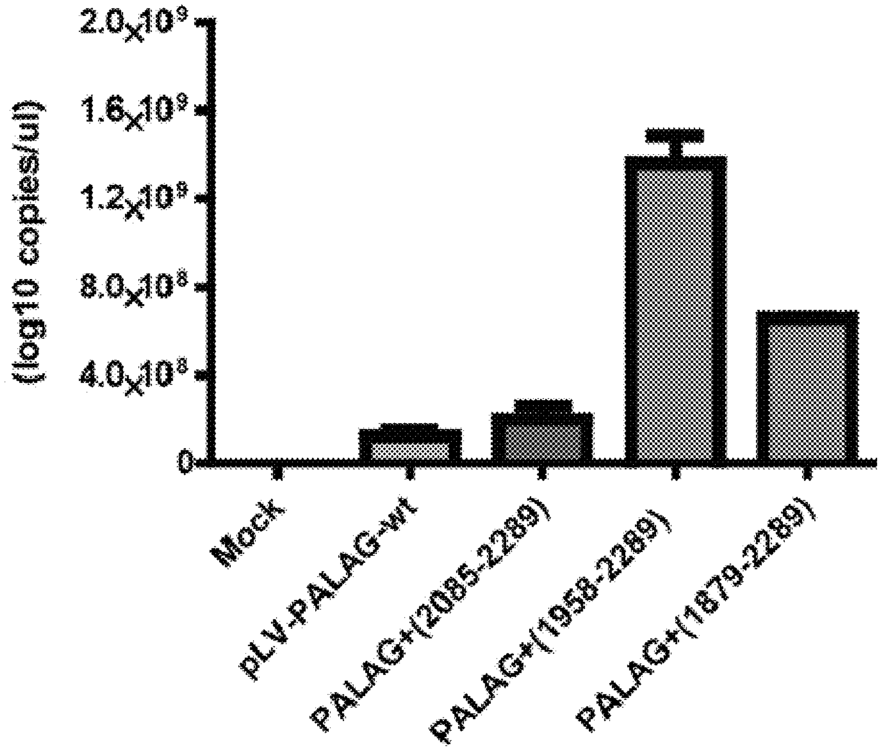
FIG. 10 is a graphical representation of the RNA packaging efficiency of lentiviral particles from 293T producer cells. Addition of nt 1958-2289 increased the packaging of viral RNA while addition of 2085-2289 had no effect and 1879-2289 had a lower effect on RNA packaging.

48 h post transfection supernatant and cells were harvested. Transfection efficacy was monitored by RT activity. Viral RNA was extracted from the cell-free supernatant and subjected to additional experiments to quantify the levels of packaged RNAs in the virions. The results for the viral RNA levels normalized to RT activities are shown in FIG. 10.

The results reveal that addition of GRPE 1958-2292 optimizes RNA packaging level in lentiviral vector pLV-mnd-PALAG+(1958-2289). However, Plasmid pLV-mnd-PALAG+(2085-2289) that doesn’t contain the P2 stem loop of GRPE/RFS has a packaging efficiency same as wild type pLV-mnd-PALAG.

Serial dilutions of MOI for lentiviruses from transfection were used to infect 293T cells and K562 (human immortalised myelogenous leukemia line). Data for K562 transduction is not shown here. The transduction efficiency in 293T was monitored 3 days post infection via measuring luciferase activity and GFP expression using flow Cytometery (FIG. 11).

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A method of enhancing the infectivity of recombinant HIV-1 particles produced from a cell transfected with an HIV-1 lentiviral vector construct, the method comprising:

administering to the cell an HIV-1 lentiviral vector construct comprising a genomic RNA packaging enhancer (GRPE) element and HIV-1 lentiviral nucleic acid sequences sufficient for reverse transcription and packaging in the cell, the GRPE element comprising a nucleic acid sequence encoding the P2 and P3 stem loops in the gag p1-p6 domain of the HIV-1 RNA wild-type genome, wherein the GRPE element maintains P2 and P3 stem loop structure and includes two or fewer nucleotide substitutions in the nucleic acid sequence encoding the P2 and P3 stem loops in the gag p1-p6 domain of the HIV-1 RNA wild-type genome, wherein the HIV-1 lentiviral nucleic acid sequences are devoid of a gag matrix/capsid/nucleocapsid (MA/CA/NC) coding sequence, wherein the presence of the GRPE in the HIV-1 lentiviral vector construct increases HIV-1 genomic RNA packaging in the recombinant HIV-1 particles produced by the transfected cell, and wherein the increase in HIV-1 genomic RNA packaging is positively correlated to the infectivity of the recombinant HIV-1 particles released from the transfected cell.

2. The method of claim 1, the GRPE element comprising the nucleic acid sequence SEQ ID NO:1 or SEQ ID NO:2.

3. The method of claim 1, wherein the HIV-1 lentiviral vector construct is an HIV-1 lentiviral transfer plasmid or an infectious HIV-1 lentiviral particle.

4. The method of claim 1, the HIV-1 lentiviral vector construct further comprising a regulatory sequence sufficient for transcription.

5. The method of claim 4, the HIV-1 lentiviral vector construct further comprising a segment that encodes a sequence of interest, wherein the regulatory sequence is operably associated with the segment that encodes the sequence of interest.

6. The method of claim 5, the sequence of interest comprising a gene of interest.

7. The method of claim 4, the regulatory sequence comprising a promoter or enhancer.

8. The method of claim 4, wherein the regulatory sequence is operably linked to a nucleic acid segment that encodes an RNAi agent or a shRNA.

9. The method of claim 4, the HIV-1 lentiviral vector construct further comprising a regulatory sequence operably linked to a nucleic acid segment that encodes a reporter gene.

10. The method of claim 9, the reporter gene comprising a detectable or selectable marker gene.

11. A method of increasing the transduction efficiency of an HIV-1 lentiviral vector construct comprising:

inserting a genomic RNA packaging enhancer (GRPE) element into an HIV-1 lentiviral vector construct, the GRPE element comprising a nucleic acid sequence encoding the P2 and P3 stem loops in the gag p1-p6 domain of the HIV-1 RNA wild-type genome, wherein the GRPE element maintains P2 and P3 stem loop structure and includes two or fewer nucleotide substitutions in the nucleic acid sequence encoding the P2 and P3 stem loops in the gag p1-p6 domain of the HIV-1 RNA wild-type genome, the HIV-1 lentiviral vector construct comprising HIV-1 lentiviral nucleic acid sequences sufficient for reverse transcription and packaging, wherein the HIV-1 lentiviral nucleic acid sequences are devoid of a gag matrix/capsid/nucleocapsid (MA/CA/NC) coding sequence; and administering the HIV-1 lentiviral vector construct including the inserted GRPE element to a first cell, wherein the presence of the GRPE element increases the HIV-1 genomic RNA packaging in recombinant HIV-1 particles released from the first cell, wherein the increased HIV-1 genomic RNA packaging is positively correlated to an increase in the transduction efficiency of the recombinant HIV-1 particles when the recombinant HIV-1 particles are administered to a second cell.

12. The method of claim 11, wherein the transduction efficiency of a recombinant HIV-1 particle is greater than the transduction efficiency of an identical recombinant HIV-1 particle not comprising a GRPE element.

13. The method of claim 11, the GRPE element comprising the nucleic acid sequence SEQ ID NO:1 or SEQ ID NO:2.

14. The method of claim 11, wherein the HIV-1 lentiviral vector construct is an HIV-1 lentiviral transfer plasmid.

15. The method of claim 11, the HIV-1 lentiviral vector construct further comprising a regulatory sequence sufficient for transcription.

16. The method of claim 15, the HIV-1 lentiviral vector construct further comprising a segment that encodes a sequence of interest, wherein the regulatory sequence is operably associated with the segment that encodes the sequence of interest.

17. The method of claim 16, the sequence of interest comprising a gene of interest.

18. The method of claim 15, the regulatory sequence comprising a promoter or enhancer.

19. The method of claim 15, wherein the regulatory sequence is operably linked to a nucleic acid segment that encodes an RNAi agent or a shRNA.

20. The method of claim 15, the HIV-1 lentiviral vector construct further comprising a regulatory sequence operably linked to a nucleic acid segment that encodes a reporter gene.

21. The method of claim 20, the reporter gene comprising a detectable or selectable marker gene.

22. The method of claim 4, wherein the regulatory sequence is operably linked to a nucleic acid segment that encodes a biologically active, immunogenic and/or antigenic protein or polypeptide, and wherein introduction of the HIV-1 lentiviral vector construct into a cell thus results in expression of the protein or polypeptide by the cell.

23. The method of claim 15, wherein the regulatory sequence is operably linked to a nucleic acid segment that encodes a biologically active, immunogenic and/or antigenic protein or polypeptide, and wherein introduction of the HIV-1 lentiviral vector construct into a cell thus results in expression of the protein or polypeptide by the cell.

* * * * *